(12) United States Patent
Choi et al.

(10) Patent No.: US 11,571,426 B2
(45) Date of Patent: Feb. 7, 2023

(54) COMPOSITIONS FOR PREVENTING OR TREATING LUPUS

(71) Applicant: CHONG KUN DANG PHARMACEUTICAL CORP., Seou (KR)

(72) Inventors: Young Il Choi, Gyeonggi-do (KR); Nina Ha, Gyeonggi-do (KR); Daekwon Bae, Gyeonggi-do (KR)

(73) Assignee: Chong Kun Dang Pharmaceutical Corp.

( * ) Notice: Subject to any disclaimer, the term of this patent is extended or adjusted under 35 U.S.C. 154(b) by 0 days.

(21) Appl. No.: 16/766,578

(22) PCT Filed: Nov. 23, 2018

(86) PCT No.: PCT/KR2018/014524
§ 371 (c)(1),
(2) Date: May 22, 2020

(87) PCT Pub. No.: WO2019/103524
PCT Pub. Date: May 31, 2019

(65) Prior Publication Data
US 2020/0368245 A1   Nov. 26, 2020

(30) Foreign Application Priority Data
Nov. 24, 2017   (KR) .................. 10-2017-0158867

(51) Int. Cl.
*A61K 31/5375*   (2006.01)
*A61P 37/02*   (2006.01)
(Continued)

(52) U.S. Cl.
CPC ........ *A61K 31/5375* (2013.01); *A61K 31/397* (2013.01); *A61K 31/495* (2013.01); *A61K 31/5377* (2013.01); *A61P 37/02* (2018.01)

(58) Field of Classification Search
CPC .............. A61K 31/5375; A61K 31/397; A61K 31/495; A61K 31/5377; A61K 31/496; A61P 37/02; A61P 37/00
(Continued)

(56) References Cited

U.S. PATENT DOCUMENTS

| 7,923,471 B2 | 4/2011 | Klimko et al. |
| 2003/0114525 A1 | 6/2003 | Kammer et al. |

(Continued)

FOREIGN PATENT DOCUMENTS

| AU | 2011348224 | 7/2013 |
| JP | 2005-533840 | 11/2005 |

(Continued)

OTHER PUBLICATIONS

Reilly et al , HDAC Inhibition in Lupus Models, Mol Med 17(5-6)417-425, May-Jun. 2011). (Year: 2011).*

(Continued)

*Primary Examiner* — Taylor V Oh
(74) *Attorney, Agent, or Firm* — Fish & Richardson P.C.

(57) ABSTRACT

The present invention relates to a pharmaceutical composition for preventing or treating lupus, containing a compound represented by a formula I, an optical isomer thereof or a pharmaceutically acceptable salt thereof as an effective component, as well as a treatment method using the compound, and use of the compound in the manufacture of a medicament for treating lupus. The pharmaceutical composition according to the present invention shows an excellent effect of preventing or treating lupus.

6 Claims, 16 Drawing Sheets

(51) Int. Cl.
  A61K 31/397   (2006.01)
  A61K 31/495   (2006.01)
  A61K 31/5377  (2006.01)
(58) Field of Classification Search
  USPC .................................................. 514/210.17
  See application file for complete search history.

(56) References Cited

U.S. PATENT DOCUMENTS

| | | | |
|---|---|---|---|
| 2005/0113373 | A1 | 5/2005 | Van Emelen et al. |
| 2005/0159470 | A1 | 7/2005 | Bressi et al. |
| 2007/0135431 | A1 | 6/2007 | Smith et al. |
| 2008/0153877 | A1 | 6/2008 | Adimoolam et al. |
| 2009/0124646 | A1 | 5/2009 | Verdonck et al. |
| 2012/0028963 | A1 | 2/2012 | Lee et al. |
| 2012/0282167 | A1 | 11/2012 | Vallot et al. |
| 2014/0163009 | A1 | 6/2014 | Luckhurst et al. |
| 2016/0083354 | A1 | 3/2016 | Lee et al. |
| 2016/0289230 | A1 | 10/2016 | Lee et al. |
| 2017/0152230 | A9 | 6/2017 | Lee et al. |
| 2018/0072671 | A1 | 3/2018 | Holson et al. |
| 2021/0077501 | A1 | 3/2021 | Choi et al. |
| 2021/0161905 | A1 | 6/2021 | Choi et al. |

FOREIGN PATENT DOCUMENTS

| | | |
|---|---|---|
| JP | 2006-512318 | 4/2006 |
| JP | 2010-514777 | 5/2010 |
| JP | 2013-518050 | 5/2013 |
| JP | 2013542994 | 11/2013 |
| JP | 2016524597 | 8/2016 |
| JP | 2016531163 | 10/2016 |
| KR | 10-2013-0115300 | 10/2013 |
| KR | 10-2014-0128886 A1 | 11/2014 |
| KR | 10-1645379 | 8/2016 |
| RU | 2252939 | 5/2005 |
| RU | 2448965 | 4/2012 |
| WO | WO 2003/068230 | 8/2003 |
| WO | 2004009536 A1 | 1/2004 |
| WO | WO 2004/043352 | 5/2004 |
| WO | WO 2006/056930 | 6/2006 |
| WO | WO 2007/039322 | 4/2007 |
| WO | WO 2008/082856 | 7/2008 |
| WO | WO 2011/091213 | 7/2011 |
| WO | WO 2012068109 | 5/2012 |
| WO | WO 2012088305 | 6/2012 |
| WO | WO 2012/106343 | 8/2012 |
| WO | 2014178606 A1 | 11/2014 |
| WO | WO 2015042418 | 3/2015 |
| WO | WO 2016/168598 | 10/2016 |
| WO | WO 2017/040564 | 3/2017 |
| WO | WO 2017/208032 | 12/2017 |
| WO | WO 2018/200608 | 11/2018 |

OTHER PUBLICATIONS

International Search Report for PCT/KR2018/014524, dated Mar. 13, 2019. 5 pages.
Fang et al, "Vorinostat Modulates the Imbalance of T Cell Subsets, Suppresses Macrophage Activity, and Ameliorates Experimental Autoimmune Uveoretinitis," NeuroMolecular Medicines, Jan. 21, 2016, 18(1):134-145.
KR Office Action in Korean Appln. No. 10-2017-0158867, dated Mar. 8, 2021, 7 pages (with Machine Translation).
RU Office Action in Russian Appln. No. 2020120706, dated Feb. 20, 2021, 24 pages (with English Translation).
PCT International Preliminary Report on Patentability in International Appln. No. PCT/KR2018/014524, dated May 26, 2020, 8 pages.
RU Office Action in Russian Appln. No. 2020120706, dated Oct. 26, 2020, 10 pages (with English Translation).
RU Search Report in Russian Appln. No. 2020120706, dated Oct. 26, 2020, 4 pages (with English Translation).
Crispin et al., "Expanded Double Negative T Cells in Patients with Systemic Lupus Erythematosus Produce IL-17 and Infiltrate the Kidneys," The Journal of Immunology, Dec. 15, 2008, 181(12):8761-8766.
Shivakumar et al., "T cell receptor alpha/beta expressing double-negative (CD4−/CD8−) and CD4+ T helper cells in humans augment the production of pathogenic anti-DNA autoantibodies associated with lupus nephritis," The Journal of Immunology, Jul. 1, 1998, 143(1):103-112.
Zickert et al., "IL-17 and IL-23 in lupus nephritis—association to histopathology and response to treatment," BMC Immunology, 2015, 16(7): 10 pages.
CA Office Action in Canadian Appln. No. 3080111, dated Jun. 4, 2021, 5 pages.
EP Extended Search Report in European Appln. No. 18881572.4, dated Jul. 2, 2021, 15 pages.
JP Office Action in Japanese Appln. No. 2020-528455, dated Jul. 6, 2021, 7 pages (with English Translation).
Mishra et al., "Histone deacetylase inhibitors modulate renal disease in the MRL-lpr/lpr mouse," The Journal of Clinical Investigation, 2003 111(4):539-552.
Regna et al., "HDAC expression and activity is upregulated in diseased lupus-prone mice," International Immunopharmacology, 2015, 29:494-503.
Regna et al., "Specific HDAC6 inhibition by ACY-738 reduces SLE pathogenesis in NZB/W mice (THER6P.858)," The Journal of Immunology, 2014, 192(1 Suppl.), 3 pages.
Reilly et al., "HDAC Inhibition in Lupus Models," Molecular Medicine, 2011, 17(5-6):417-425.
Reilly et al., "Modulation of renal disease in MRL/lpr mice by suberoylanilide hydroxamic acid," The Journal of Immunology, 2004, 173:4171-4178.
Vieson et al., "Selective HDAC6 Inhibition in Systemic Lupus Erythematosus," Dissertation submitted to the faculty of the Virginia Polytechnic Institute and State University in partial fulfillment of the requirements for the degree of Doctor of Philosophy in Biomedical and Veterinary Sciences, Nov. 28, 2016, 42 pages.
Annoni et al., "Extracellular matrix composition in COPD," European Respiratory Journal, 2012, 40(6):1362-1373.
AU Office Action in Australian Appln. No. 2019224697, dated Feb. 19, 2021, 4 pages.
AU Office Action in Australian Appln. No. 2019252496, dated May 24, 2021, 3 pages.
Bron et al., "Grading of corneal and conjunctival staining in the context of other dry eye tests," Cornea, Oct. 2003, 22(7):640-650.
CA Office Action in Canadian Appln. No. 3088956, dated Aug. 24, 2021, 6 pages.
CA Office Action in Canadian Appln. No. 3092815, dated Nov. 9, 2021, 4 pages.
Courtney et al., "The role of epithelial-mesenchymal transition in chronic obstructive pulmonary disease," Cells Tissues Organs, 2017, 203:99-104.
EP Extended Search Report in European Appln. No. 19757638.2, dated Oct. 28, 2021, 9 pages.
EP Extended Search Report in European Appln. No. 19784737.9, dated Dec. 14, 2021, 10 pages.
IN Office Action in Indian Appln. No. 202117020551, dated Oct. 25, 2021, 5 pages (with English Translation).
JP Office Action in Japanese Appln. No. 2020-543933, dated Jul. 27, 2021, 10 pages (with English Translation).
JP Office Action in Japanese Appln. No. 2020-550107, dated Sep. 14, 2021, 6 pages (with English Translation).
Ling et al., "Design and Synthesis of C3-Substituted β-Carboline-Based Histone Deacetylase Inhibitors with Potent Antitumor Activities," ChemMedChem, 2017, 12(9):646-651.
Liu et al., "Effect of HDACi Givinostat in Treating Experimental Ocular Autoimmunity," Abstract, ARVO Annual Meeting Abstract, Investigative Ophthalmology & Visual Science, 2015, 56(7), 2 pages.

(56) References Cited

OTHER PUBLICATIONS

Mashkovsky, "Medicaments," 14th edition, revised, corrected and supplemented, Doctors' Manual, vol. 1, Moscow, OOO Novaya Volna, Publisher S.B.Divov, 2001, 6 pages (with Partial Translation; p. 11).

Massingale et al., "Analysis of inflammatory cytokines in the tears of dry eye patients," Cornea, 2009, 28(9):1023-1027.

Na et al., "Correlations between tear cytokines, chemokines, and soluble receptors and clinical severity of dry eye disease," Investigative Ophthalmology & Visual Science, 2012, 53(9):5443-5450.

Orlov-Morozov, "Exacerbation of ankylosing spondylitis after low-doses methotrexate therapy," Almanac of Clinical Medicine, 2014, (35):77-83, retrieved from: URL<https://doi.org/10.18786/2072-0505>, 15 pages (with English Translation).

PCT International Preliminary Report on Patentability in International Appln. No. PCT/KR2019/004227, dated Oct. 13, 2020, 7 pages.

PCT International Search Report and Written Opinion in International Appln. No. PCT/IB2020/059919, dated Feb. 1, 2021, 9 pages.

PCT International Search Report and Written Opinion in International Appln. PCT/KR2019/013389, dated Jan. 28, 2020, 10 pages.

PCT International Search Report in International Appln. No. PCT/KR2019/001989, dated May 30, 2019, 5 pages.

PCT International Search Report in International Appln. No. PCT/KR2019/004227, dated Jul. 19, 2019, 4 pages.

PCT Written Opinion in International Appln. No. PCT/KR2019/001989, dated May 30, 2019, 7 pages.

PCT Written Opinion in International Appln. No. PCT/KR2019/004227, dated Jul. 19, 2019, 6 pages.

Ratay et al., "Controlled Release of an HDAC Inhibitor for Reduction of Inflammation in Dry Eye Disease," Acta Biomaterialia, Sep. 2018, 71:261-270.

RU Office Action in Russian Appln. No. 2020130792, dated Feb. 19, 2021, 26 pages (with English Translation).

RU Office Action in Russian Appln. No. 2020136593, dated Apr. 30, 2021, 15 pages (with English Translation).

RU Office Action in Russian Appln. No. 2021113227, dated Oct. 25, 2021, 18 pages (with English Translation).

SK Ajigaitkanova, "Evidence-Based Diagnosis and Treatment of Certain Forms of Rheumatic Diseases," Teaching Manual—Study Guide, N.I. Pirogov Russian National Research Medical University, 2013, 55 pages (with Partial Translation; p. 5).

Vishwakarma et al., "Tubastatin, a selective histone deacetylase 6 inhibitor shows anti-inflammatory and anti-rheumatic effects," International Immunopharmacology, Mar. 27, 2013, 16:72-78.

Vojinovic et al., "HDAC Inhibition in Rheumatoid Arthritis and Juvenile Idiopathic Arthritis," Molecular Medicine, May-Jun. 2011, 17(5-6):397-403.

Wei et al., "Norisoboldine alleviates joint destruction in rats with adjuvant-induced arthritis by reducing RANKL, IL-6, $PGE_2$, and MMP-13 expression," Acta Pharmacologica Sinica, Feb. 11, 2013, 34:403-413.

Altundag et al., "Synergistic Effects of Methotrexate and Suberoylanilide Hydroxamic Acid in Triggering Apoptosis of Chronic Myeloid Leukemia Cells," UHOD—Uluslararasi Hematoloji-Onkoloji Dergisi, International Journal of Hematology and Oncology, 2015, 25(1), 12 pages.

AU Office Action in Australian Appln. No. 2019359017, dated Mar. 24, 2022, 8 pages.

Bastian et al., "The sequence of application of methotrexate and histone deacetylase inhibitors determines either a synergistic or an antagonistic response in childhood acute lymphoblastic leukemia cells," Leukemia, 2011, 25:359-361.

Choi et al., "Vorinostat plus tacrolimus/methotrexate to prevent GVHD after myeloablative conditioning, unrelated donor HCT," Blood, 2017, 130(15):1760-1767.

EP Extended Search Report in European Appln. No. 19871546.8, dated May 23, 2022, 7 pages.

JP Office Action in Japanese Appln. No. 2021-520184, dated Apr. 12, 2022, 6 pages (with English Translation).

Shin et al., "CKD-506, a novel inhibitor of histone deacetylase 6 (HDAC6) has a therapeutic potential in rheumatoid arthritis and inflammatory bowel disease," Abstract No. 82, Arthritis Rheumatol., 2017, 69(suppl 10), 3 pages.

Cannon, Burger's Medicinal Chemistry and Drug Discovery, vol. I: Principles and Practice, 5th ed., Wiley-Interscience, 1995, Chapter 19, pp. 783-802.

Sheridan, "The Most Common Chemical Replacement in Drug-Like Compounds," J. Chem. Inf. Comput. Sci., 2002, 42:103-108.

U.S. Office Action in United States U.S. Appl. No. 17/284,591, dated Jul. 8, 2022, 26 pages.

Vojinovic et al. "Safety and Efficacy of an Oral Histone Deacetylase Inhibitor in Systemic-Onset Juvenile Idiopathic Arthritis," Arthritis & Rheumatism, 2011, 63(5)1452-1458.

Webmd.Com, Bruce, [Online], "Rheumatology and Rheumatic Diseases," Medically Reviewed on May 15, 2021, [Retrieved on or before Jul. 8, 2022], retrieved from: URL<https://www.webmd.com/rheumatoid-arthritis/an-overview-of-rheumatic-diseases>, 17 pages.

U.S. Appl. No. 16/970,292, filed Aug. 14, 2020, Young Il Choi.

U.S. Appl. No. 17/046,402, filed Oct. 9, 2020, Young Il Choi.

U.S. Appl. No. 17/284,591, filed Apr. 12, 2021, Young Il Choi.

U.S. Appl. No. 17/768,571, filed Apr. 13, 2022, Young Il Choi.

CN Office Action in Chinese Appln. No. 201880075639.2, dated Sep. 5, 2022, 13 pages (with English Translation).

Regna et al., "Specific HDAC6 inhibition by ACY-738 reduces SLE pathogenesis in NZB/W mice," Clinical Immunology, 2016, 162:58-73.

Vieson et al., "Treatment with a selective histone deacetylase 6 inhibitor decreases lupus nephritis in NZB/W mice," Histol. Histopathol., 2017, 32(12):1317-1332.

* cited by examiner

COMPOSITIONS FOR PREVENTING OR TREATING LUPUS

TECHNICAL FIELD

The present invention relates to a pharmaceutical composition for preventing or treating lupus, comprising a compound represented by a formula I, an optical isomer thereof or a pharmaceutically acceptable salt thereof as an effective component, as well as a treatment method using the compound, and use of the compound in the manufacture of a medicament for treating lupus.

BACKGROUND ART

Lupus is an autoimmune disease related to antibodies attacking connective tissues, wherein it is also associated with a production of antinuclear antibodies, i.e., a circulating immune complex, as well as with an activation of a complement system. This disease is systemic, such that it may occur in all organ systems and also cause severe tissue injuries. Patients with lupus may also produce auto-antibodies having anti-DNA, anti-Ro and anti-platelet specificities, and cause the occurrence of diseases such as glomerulonephritis, arthritis, serositis, neonatal complete heart block or haematological abnormality.

Unless treated, lupus may become fatal because it starts attacking skin and joints and progresses into attacking even internal organs, e.g., lung, heart and kidney, out of which a kidney disease is of most concern. A kidney injury, which is measured by means of the amount of proteinuria in urine, is one of acute injury parts associated with the pathogenicity of lupus and accounts for 50% or more of the mortality and incidence rate of the lupus disease.

For now, there has been no infallible remedy for lupus patients. In a practical viewpoint, doctors generally use a number of immunosuppressants, e.g., a high dose of corticosteroid, prednisone, azathioprine or cyclophosphamide, wherein there is a problem in that a considerable number of such drugs have potentially harmful side effects to patients under treatment.

Prior Art References
Patent Document
Korea Patent Application Publication No. 2014-0128886

DISCLOSURE OF INVENTION

Technical Problem

The objective of the present invention is to provide a pharmaceutical composition for preventing or treating lupus, comprising a compound represented by a following formula I, an optical isomer thereof or a pharmaceutically acceptable salt thereof as an effective component.

Another objective of the present invention is to provide a method for treating lupus, wherein the method comprises administering a therapeutically effective amount of the said compound.

Another objective of the present invention is to provide use of the compound in the manufacture of a medicament for treating lupus.

Solution to Problem

This will be described in detail as follows. Meanwhile, each description and embodiment form disclosed in the present invention may be applied to other descriptions and embodiment forms thereof, respectively. In other words, all combinations of various elements disclosed in the present invention fall within the scope of the present invention. Also, it cannot be seen that the scope of the present invention is limited to the specific description described below.

The present invention provides a pharmaceutical composition for preventing or treating lupus, comprising a compound represented by a following formula I, an optical isomer thereof or a pharmaceutically acceptable salt thereof as an effective component:

[Formula I]

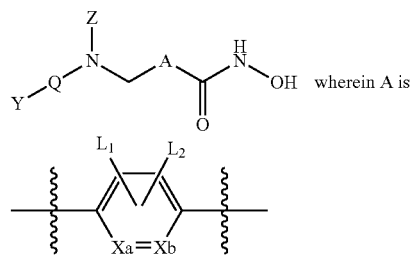 wherein A is

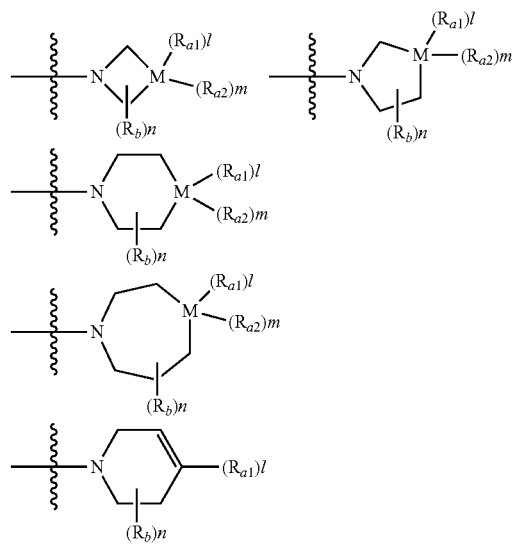

$Xa$ and $Xb$ are each independently CH or N, $L_1$ and $L_2$ are each independently hydrogen, halogen, —$CF_3$ or —$C_{1-3}$ straight or branched chain alkyl, Q is C(=O), S(=O)$_2$, S(=O) or C(=NH), Y is selected from a following group:

M is C, N, O, S or S(=O)$_2$, wherein, at this time, in case M is C, 1 and m are 1; in case M is N, 1 is 1 and m is 0; and in case M is 0, S or S(=O)$_2$, 1 and m are 0, $R_{a1}$ and $R_{a2}$ are each independently hydrogen; hydroxy; —$C_{1-4}$ straight or branched chain alkyl, which is unsubstituted or substituted with at least one halogen; —$C_{1-4}$ straight or branched chain alcohol; benzhydryl; —$C_{1-4}$ straight or branched chain alkyl, which is substituted with a saturated or unsaturated 5- to 7-membered heterocyclized compound comprising 1 to 3 heteroatoms of N, O or S as a ring member, wherein, at this time, the heterocyclized compound may be unsubstituted or at least one hydrogen may be optionally substituted with OH, OCH$_3$, CH$_3$, CH$_2$CH$_3$ or halogen; a saturated or unsaturated 5- to 7-membered heterocyclized compound comprising 1 to 3 heteroatoms of N, O or S as a ring member, wherein at this time, the heterocyclized compound may be unsubstituted or at least one hydrogen may be optionally substituted with OH, OCH$_3$, CH$_3$, CH$_2$CH$_3$ or halogen; phenyl, wherein it is unsubstituted or at least one hydrogen is substituted with halogen, C$_{1-4}$ alkoxy, C$_{1-2}$ alkyl or hydroxy; benzyl, wherein it is unsubstituted or at least one hydrogen is substituted with halogen, C$_{1-4}$ alkoxy, C$_{1-2}$ alkyl or hydroxy; —S(=O)$_2$CH$_3$; halogen; —C$_{1-6}$ straight or branched chain alkoxy; —C$_{2-6}$ alkoxyalkyl; —C(=O)R$_x$, wherein R$_x$ is straight or branched chain C$_{1-3}$ alkyl or C$_{3-10}$ cycloalkyl;

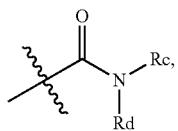

wherein R$_c$ and R$_d$ are each independently hydrogen, C$_{1-3}$ straight or branched chain alkyl; and

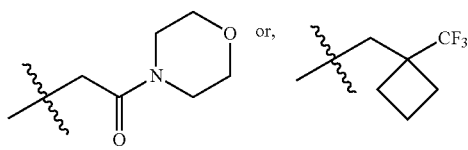 [SMILES: *CC(=O)N1CCOCC1 ; *CC1(C(F)(F)F)CCC1]

n is an integer of 0, 1 or 2,

R$_b$ is hydrogen; hydroxy; —C$_{1-6}$ straight or branched chain alkyl, wherein it is unsubstituted or at least one hydrogen is substituted with halogen; —C(=O)CH$_3$; —C$_{1-4}$ straight or branched chain hydroxyalkyl; —C$_{1-6}$ straight or branched chain alkoxy; —C$_{2-6}$ straight or branched chain alkoxyalkyl; —CF$_3$; halogen; or

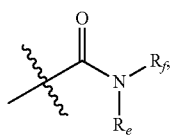

R$_e$ and R$_f$ are each independently hydrogen or —C$_{1-3}$ straight or branched chain alkyl, Z is selected from a following group:

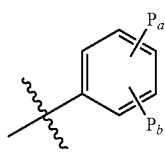 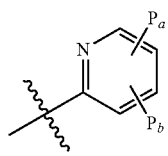

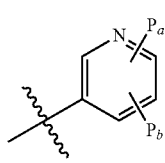 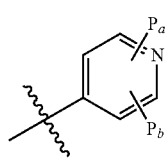

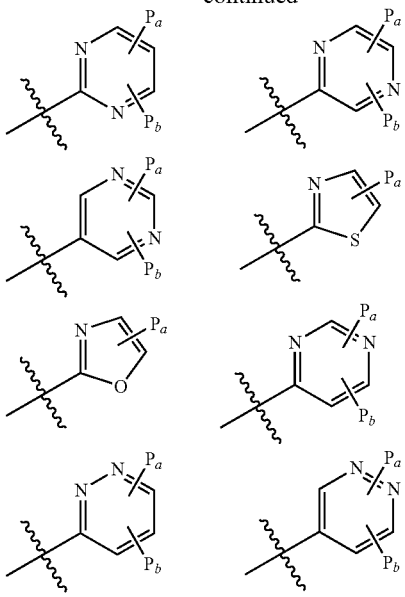

P$_a$ and P$_b$ are each independently

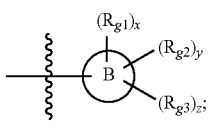

hydrogen; hydroxy; —C$_{1-4}$ straight or branched chain alkyl, wherein it is unsubstituted or at least one hydrogen is substituted with halogen; halogen; —CF$_3$; —OCF$_3$; —CN; —C$_{1-6}$ straight or branched chain alkoxy; —C$_{2-6}$ straight or branched chain alkyl alkoxy; —CH$_2$F; or —C$_{1-3}$ alcohol, wherein

is phenyl, pyridine, pyrimidine, thiazole, indole, indazole, piperazine, quinoline, furan, tetrahydropyridine, piperidine or a ring selected from a following group:

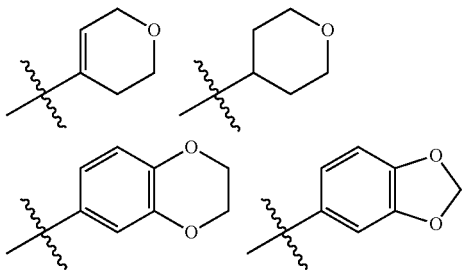

x, y and z are each independently an integer of 0 or 1,

R$_{g1}$, R$_{g2}$ and R$_{g3}$ are each independently hydrogen; hydroxy; —C$_{1-3}$ alkyl; —CF$_3$; —C$_{1-6}$ straight or branched chain alkoxy; —C$_{2-6}$ straight or branched chain alkyl alkoxy; —C(=O)CH$_3$; —C$_{1-4}$ straight or branched chain hydroxyalkyl; —N(CH$_3$)$_2$; halogen; phenyl; —S((=O)$_2$)CH$_3$; or selected from a following group:

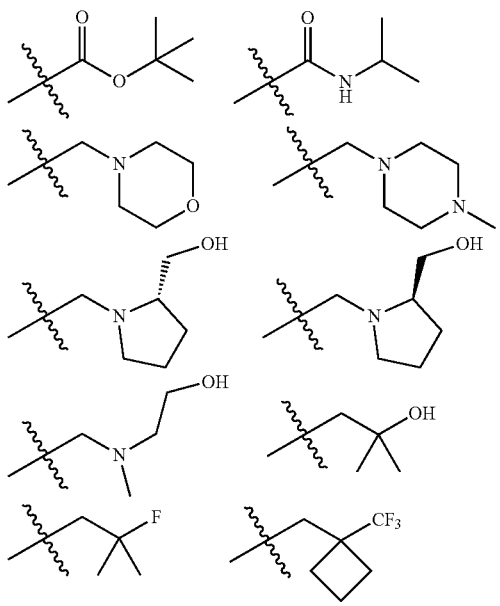

A compound represented by a formula I according to the present invention may be a compound represented by a following formula Ia:

[Formula Ia]

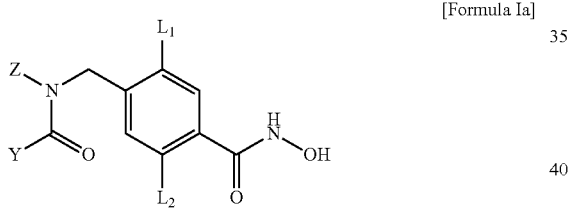

wherein
L$_1$ and L$_2$ are each independently hydrogen or halogen,
Y is

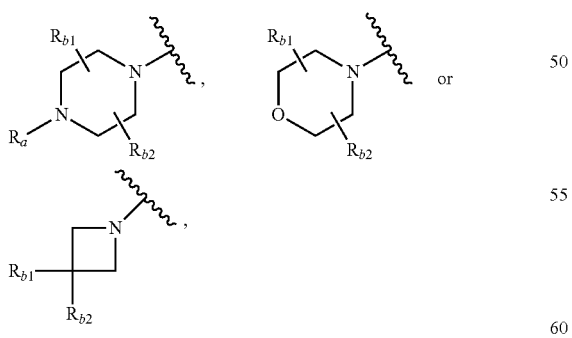

Z is phenyl or pyridinyl, wherein at least one hydrogen of phenyl or pyridinyl may be substituted with halogen, CF$_3$ or CF$_2$H.

According to a specific embodiment of the present invention, the compound represented by the formula Ia above is a compound described in a following table:

TABLE 1

| Compound | Structure |
|---|---|
| 255 | ![structure] |
| 280 | ![structure] |
| 374 | ![structure] |
| 416 | ![structure] |
| 461 | ![structure] |
| 476 | ![structure] |

TABLE 1-continued

| Compound | Structure |
|---|---|
| 500 | [structure with fluorobenzyl, morpholine carboxamide, and N-hydroxybenzamide groups] |
| 530 | [structure with fluorophenyl, morpholine carboxamide, and N-hydroxybenzamide groups] |
| 532 | [structure with trifluoromethylphenyl, morpholine carboxamide, fluoro, and N-hydroxybenzamide groups] |

In the present invention, the compound represented by the formula I above may be prepared by means of a method disclosed in Korea Unexamined Patent Application Publication No. 2014-0128886, but is not limited thereto.

In the present invention, a pharmaceutically acceptable salt means a salt conventionally used in an industry of medicine, e.g., an inorganic ion salt prepared from calcium, potassium, sodium, magnesium and the like; an inorganic acid salt prepared from hydrochloric acid, nitric acid, phosphoric acid, bromic acid, iodic acid, perchloric acid, sulfuric acid and the like; an organic acid salt prepared from acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbric acid, carbonic acid, vanillic acid, hydroiodic acid, etc.; a sulphonic acid salt prepared from methanesulfonic acid, ethanesulfonic acid, benzenesulfonic acid, p-toluenesulfonic acid, naphthalenesulfonic acid and the like; amino acid salt prepared from glycine, arginine, lysine, etc.; amine salt prepared from trimethylamine, triethylamine, ammonia, pyridine, picoline, etc.; and the like, but the types of salt meant in the present invention are not limited to those listed salts.

As used herein, a term "lupus" is an autoimmune disease related to antibodies attacking connective tissues, wherein it comprises a chronic inflammatory autoimmune disease characterized by a presence of autoantibody, rash, mouth ulcer, serositis, neurological disorder, low blood cell count, joint pain and swelling. Unless otherwise noted, the term "lupus" in the present invention has a conventional meaning used in the technical field to which the present invention pertains. In the present invention, lupus comprises systemic lupus erythematosus (SLE), systemic lupus, discoid lupus, drug induced lupus, neonatal lupus or the like, but may further comprise various additional types of lupus in a non-limiting way. Also, chronic nephritis such as lupus nephritis or glomerulonephritis may be caused by lupus.

In the present invention, the term "systemic lupus erythematosus (SLE)" has a conventional meaning used in the technical field to which the present invention pertains. The SLE is a polyphyletic autoimmune disease, wherein an antinuclear antibody including an anti-dsDNA antibody occurs, and an antigen-antibody immune complex is produced and settles in a small vessel, thus possibly causing inflammation and injury in various organs including a basement membrane of skin or kidney.

In an embodiment of the present invention, it was identified that compounds 255, 280, 374, 416, 461, 476, 500, 530 or 532 represented by a formula Ia had an excellent effect of suppressing an in-vitro production of inflammatory molecules such as TNFα, etc. (FIG. 1), suppressing proliferation of reactive T cells (FIG. 2), and improving a function of regulatory T cells (FIG. 3).

Also, it was identified that the compound 374 according to the present invention improved a survival rate of an SLE disease mouse (FIG. 5), reduced an incidence rate of proteinuria (FIG. 6), a concentration of anti-dsDNA antibodies (FIG. 8), and a level of IgG and C3 infiltrations in kidney (FIG. 12), reduced a level of IL-10, IL-12, IL-15, IL-17A, TNFα and IL-22 in serum cytokine (FIG. 13), decreased a level of CXCL10 and CCL2 (FIG. 14), increased a level of TGF-β (FIG. 13), and reduced a ratio of CD4−CD8− double negative T cells, a ratio of CD4+CD8− cellular level to CD4−CD8+ cellular level (FIG. 15), a ratio of CD4+T-bet+/CD4+GATA3+(FIG. 16), a ratio of CD4+CD25+ cellular level to CD4+ cellular level (FIG. 17) and a CD138+ cellular level (FIG. 19).

A pharmaceutical composition according to the present invention may further comprise at least one type of a pharmaceutically acceptable carrier, in addition to the compound represented by the formula I above, the optical isomer thereof or the pharmaceutically acceptable salt thereof, for the purpose of administration. As the pharmaceutically acceptable carrier, saline solution, sterilized water, Ringer's solution, buffered saline, dextrose solution, maltodextrin solution, glycerol, ethanol and a combination of at least one component thereof may be used, wherein other conventional additives such as antioxidant, buffer solution, bacteriostatic agent, etc., may be also added thereto, if needed. Also, the pharmaceutical composition according to the present invention may be formulated into an injectable dosage form such as aqueous solution, suspension, emulsion, etc., pill, capsule, granule or tablet in such a way that diluent, dispersing agent, surfactant, binder and lubricant are further added thereto. Thus, the composition according to the present invention may be a patch, liquid medicine, pill, capsule, granule, tablet, suppository, etc. These preparations may be formulated by means of a conventional method used for formulation in the technical field to which the present invention pertains according to each disease and/or component, or a method disclosed in Remington's Pharmaceutical Science (the latest version), Mack Publishing Company, Easton Pa.

A non-limiting example of a preparation for oral administration using the pharmaceutical composition according to the present invention may be a tablet, troche, lozenge, water soluble suspension, oil suspension, prepared powder, granule, emulsion, hard capsule, soft capsule, syrup, elixir or the like. To formulate the pharmaceutical composition according to the present invention into a preparation for oral administration, a binder such as lactose, saccharose, sorbitol, mannitol, starch, amylopectin, cellulose, gelatin or the like; an excipient such as dicalcium phosphate, etc.; a disintegrant such as maize starch, sweet potato starch or the like; a lubricant such as magnesium stearate, calcium stearate, sodium stearyl fumarate, polyethylene glycol wax or the like; and so on may be used, and a sweetening agent, flavoring agent, syrup, etc., may be also used. Furthermore, in case of the capsule, a liquid carrier such as fatty oil, etc. may be further used in addition to the above-mentioned materials.

A non-limiting example of a parenteral preparation using the pharmaceutical composition according to the present invention may be an injectable solution, suppository, powder for respiratory inhalation, aerosol preparation for spray, ointment, powder for application, oil, cream, etc. To formulate the pharmaceutical composition according to the present invention into a preparation for parenteral administration, a sterilized aqueous solution, nonaqueous solvent, suspension, emulsion, freeze-dried preparation, external preparation, etc. may be used. As the said nonaqueous solvent and suspension, a vegetable oil such as propylene glycol, polyethylene glycol and olive oil; an injectable ester such as ethyl oleate; and so on may be used.

In case of formulating the pharmaceutical composition according to the present invention into the injectable solution, the pharmaceutical composition according to the present invention may be prepared into solution or suspension, in such a way that the inventive composition is mixed in water with stabilizer or buffer, and then the solution or suspension may be formulated into a unit administration form of ampoule or vial.

In case of formulating the pharmaceutical composition according to the present invention into the aerosol preparation, the inventive composition may be mixed together with additives, including a propellant, etc., such that a water-dispersed concentrate or wet powder may be dispersed.

In case of formulating the pharmaceutical composition according to the present invention into ointment, cream, powder for application, oil, external skin preparation, etc., the inventive composition may be formulated into a preparation in such a way that animal oil, vegetable oil, wax, paraffin, starch, tragacanth, cellulose derivative, polyethylene glycol, silicon, bentonite, silica, talc, zinc oxide, etc. are used as a carrier.

A daily dosage of a compound represented by a formula I according to the present invention, an optical isomer thereof or a pharmaceutically acceptable salt thereof may fall, for example, in a range of about 0.1 to 10,000 mg/kg, in a range of about 1 to 8,000 mg/kg, in a range of about 5 to 6,000 mg/kg, or in a range of about 10 to 4,000 mg/kg, preferably in a range of about 50 to 2,000 mg/kg, but is not limited thereto, wherein such dosage may be also administered once a day or divided into several times a day for administration.

A pharmaceutically effective amount and effective dosage of the pharmaceutical composition according to the present invention may be diversified by means of a method for formulating the pharmaceutical composition into a preparation, an administration mode, an administration time and/or administration route, etc., and may be diversified according to various factors including a type and degree of reactions to be achieved by means of an administration of the pharmaceutical composition, a type of an individual to be administered, age, weight, general health condition, a symptom or severity of disease, gender, diet, excretion, a component of other drug compositions used together at the same time or different times for the corresponding individual, and so on, as well as other similar factors well known in a field of medicine, wherein those skilled in the art may easily determine and prescribe a dosage effective for targeted treatment.

In case of the administration of the pharmaceutical composition according to the present invention, it may be administered once a day or divided into several times a day for administration. The pharmaceutical composition according to the present invention may be administered as an individual therapeutic agent or in combination with other therapeutic agents, and may be also administered sequentially or simultaneously with a conventional therapeutic agent. Considering all the factors above, the pharmaceutical composition according to the present invention may be administered by an amount, which can show the maximum effect with the minimum amount without any side effect, wherein such amount may be easily determined by those skilled in the art to which the present invention pertains.

The pharmaceutical composition according to the present invention may show an excellent effect even when used alone, but may be further used in combination with various methods such as hormone therapy, drug treatment, etc. so as to increase a therapeutic efficiency.

The present invention also provides a method for treating lupus, wherein the method comprises administering a therapeutically effective amount of the compound represented by the formula I above, the isomer thereof or the pharmaceutically acceptable salt thereof into an individual in need.

As used herein, the term "therapeutically effective amount" refers to an amount of the compound represented by the formula I above, which is effective in treating lupus.

In the treatment method according to the present invention, a suitable total daily dose of the compound represented by the formula I above, the isomer thereof or the pharmaceutically acceptable salt thereof may be determined by a doctor in charge within the range of correct medical decision, and may fall, for example, in a range of about 0.1 to 10,000 mg/kg, in a range of about 1 to 8,000 mg/kg, in a range of about 5 to 6,000 mg/kg, or in a range of about 10 to 4,000 mg/kg, and preferably such dose in a range of about 50 to 2,000 mg/kg may be administered once a day or divided into several times a day for administration. However, for the purpose of the present invention, it is preferable that a specific, therapeutically effective amount for a certain patient is differently applied depending on various factors including a type and degree of reactions to be achieved, a specific composition including whether other preparations are used or not in some cases, a patient's age, weight, general health condition, gender and diet, an administration time, an administration route and a secretion rate of the composition, a treatment period, and a drug used together or simultaneously with the specific composition, as well as other similar factors well known in a field of medicine.

The method for treating lupus according to the present invention comprises not only dealing with the disease itself before expression of its symptoms, but also inhibiting or avoiding such symptoms by administering the compound represented by the formula I above. In managing the disease, a preventive or therapeutic dose of a certain active component may vary depending on characteristics and severity of the disease or condition, and a route in which the active component is administered. The dose and a frequency thereof may vary depending on an individual patient's age, weight and reactions. A suitable dose and usage may be easily selected by those skilled in the art, naturally considering such factors. Also, the method for treating lupus according to the present invention may further comprise administering a therapeutically effective dose of an additional active agent, which is helpful in treating the disease, along with the compound represented by the formula I above, wherein the additional active agent may show a synergy effect or an additive effect together with the compound of the formula I above.

The present invention also provides a use of the compound represented by the formula I above, the isomer thereof or the pharmaceutically acceptable salt thereof in the manufacture of a medicament for treating lupus.

The compound represented by the formula I above for the manufacture of a medicament may be combined with a pharmaceutically acceptable adjuvant, diluent, carrier, etc., and may be prepared into a composite agent together with other active agents, thus having a synergy action.

The matters mentioned in the inventive pharmaceutical composition, the treatment method and the use are equally applied, if not contradictory to each other.

Advantageous Effects of Invention

A pharmaceutical composition comprising a compound represented by a formula I according to the present invention, an optical isomer thereof or a pharmaceutically acceptable salt thereof may show an excellent effect of treating lupus, such that the pharmaceutical composition may be widely used for prevention or treatment of lupus.

MODE FOR THE INVENTION

Figure 1:
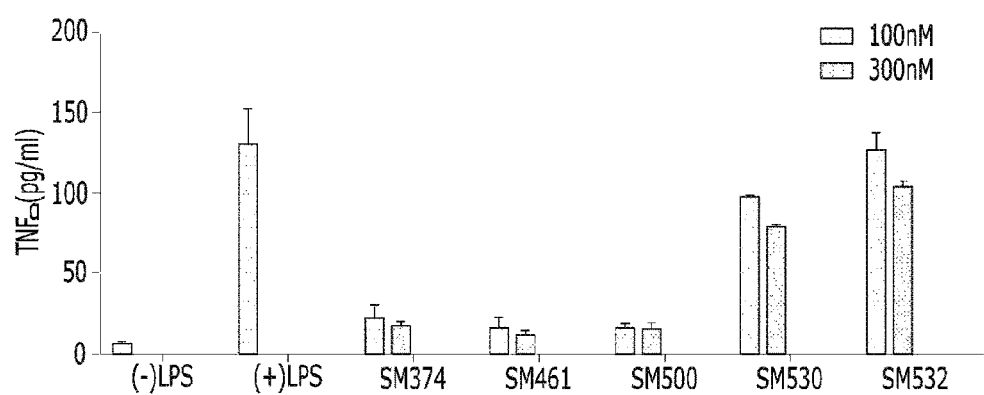
FIG. 1 shows results of identifying an effect of the inventive pharmaceutical composition on suppressing TNFα secretion.

Hereinafter, the present invention will be described in more detail according to preparation examples and embodiments. However, these preparation examples and embodiments are provided only for the purpose of illustrating the present invention, and thus the present invention is not limited thereto.

Compounds 255, 280, 374, 416, 461, 476, 500, 530 or 532 according to the present invention were prepared by means of a method described in Korea Unexamined Patent Application Publication No. 2014-0128886, and specific preparation examples are described below. A newly named formula in each preparation example is mentioned within a corresponding preparation example only, and the formulas mentioned in at least two preparation examples are independently used in each preparation example.

Preparation Example 1. Synthesis of compound 255 {N-(3-bromophenyl)-N-(4-(hydroxycarbamoyl)benzyl)morpholine-4-carboxamide}

[Step 1] Synthesis of methyl 4-((N-(3-bromophenyl)morpholine-4-carboxamido)methyl)benzoate

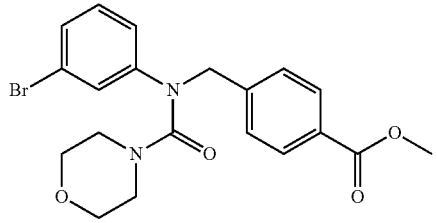 [SMILES: COC(=O)c1ccc(CN(C(=O)N2CCOCC2)c2cccc(Br)c2)cc1]

Methyl 4-(((3-bromophenyl)((4-nitrophenoxy)carbonyl) amino)methyl)benzoate (1.5 g, 3.09 mmol) was dissolved in acetonitrile (50 ml), and then potassium carbonate (1.28 g, 9.3 mmol) and morpholine (0.40 mL, 4.64 mmol) were slowly added thereto. After that, a temperature of a resulting mixture was slowly raised up to 80° C., and then the resulting mixture was stirred for three hours at that temperature. The temperature was cooled down to room temperature, then dimethylformamide (50 ml) was further added thereto, then the temperature was raised up to 80° C. again, and then the resulting mixture was stirred for five hours at that temperature. After a reaction was completed, an organic layer was washed with saturated ammonium chloride aqueous solution three times, then dried by means of sodium sulfate and filtered, and then a filtrate was concentrated under reduced pressure. A concentrate was purified via column chromatography (silicon dioxide; ethyl acetate/hexane=0-50%), such that a title compound (0.45 g, 33.6%) was obtained in a transparent oil form.

[Step 2] Synthesis of N-(3-bromophenyl)-N-(4-(hydroxycarbamoyl)benzyl)morpholine-4-carboxamide

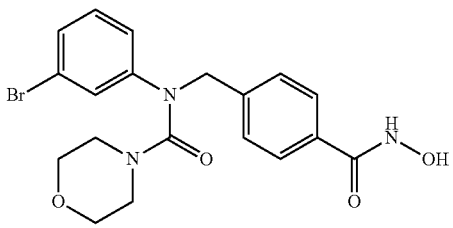 [SMILES: O=C(NO)c1ccc(CN(C(=O)N2CCOCC2)c2cccc(Br)c2)cc1]

Methyl 4-((N-(3-bromophenyl)morpholine-4-carboxamido)methyl)benzoate (0.05 g, 0.12 mmol) was dissolved in methanol (2 ml), and then hydroxylamine hydrochloric acid (0.040 g, 0.58 mmol) was slowly added thereto. After that, potassium hydroxide (0.065 g, 1.15 mmol) was inserted into a resulting mixture, and stirred at room temperature for ten minutes, and then hydroxylamine (50.0 wt % aqueous solution, 0.14 mL, 2.31 mmol) was inserted thereinto. After the resulting mixture was stirred at room temperature for a day, an organic solvent was concentrated under reduced pressure, and then neutralized with the addition of 2N hydrochloric acid. Then, an organic layer was washed with saturated sodium chloride aqueous solution three times, and then dried by means of anhydrous sodium sulfate and filtered. After that, a filtrate was concentrated under reduced pressure, and then a concentrate was purified via column chromatography (silicon dioxide; ethyl acetate/hexane=0-80%), such that a title compound (0.036 g, 72%) was obtained in a white solid form.

$^1$H NMR (400 MHz, CDCl$_3$-d$_6$) δ 7.63 (d, 2H, J=7.8 Hz), 7.27-7.20 (m, 4H), 7.13 (t, 1H, J=7.8 Hz), 6.96 (d, 1H, J=7.1 Hz), 4.83 (s, 2H), 3.49 (brs, 4H), 3.23 (brs, 4H); MS (ESI) m/z 436 (M$^+$+H).

Preparation Example 2. Synthesis of compound 280 {N-(4-(hydroxycarbamoyl)benzyl)-N-(pyridine-2-yl)morpholine-4-carboxamide}

[Step 1] Synthesis of methyl 4-((pyridine-2-ylamino)methyl)benzoate

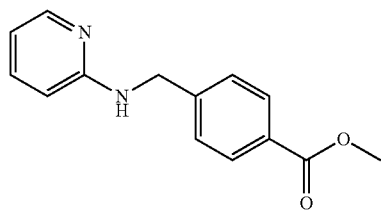 [SMILES: COC(=O)c1ccc(CNc2ccccn2)cc1]

Pyridine-2-amine (0.2 g, 2.13 mmol) was dissolved in methanol (10 mL), and then methyl 4-formylbenzoate (0.35 g, 2.13 mmol) was added thereto. After a resulting mixture was stirred at room temperature for 20 minutes, sodium cyanoborohydride (0.13 g, 2.13 mmol) and acetic acid (0.12 mL. 2.13 mmol) were slowly added thereto, and then stirred at room temperature for five hours. The resulting mixture was washed with saturated sodium chloride aqueous solution three times, then an organic layer was dried by means of sodium sulfate and filtered, and then a filtrate was concentrated under reduced pressure. A concentrate was purified via column chromatography (silicon dioxide; ethyl acetate/hexane=0-30%), such that a title compound (0.10 g, 19%) was obtained in a transparent oil form.

$^1$H NMR (400 MHz, CDCl$_3$) δ 8.17 (d, 1H, J=5.8 Hz), 8.06 (d, 2H, J=8.4 Hz), 7.66 (t, 1H, J=7.8 Hz), 7.44 (d, 2H, J=8.0 Hz), 6.76 (t, 1H, J=6.7 Hz), 6.58 (d, 1H, J=8.6 Hz), 4.67 (d, 2H, J=6.0 Hz), 3.92 (s, 3H).

[Step 2] Synthesis of methyl 4-((((4-nitrophenoxy)carbonyl)(pyridine-2-yl)amino)methyl)benzoate

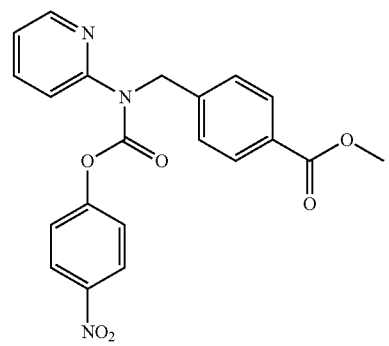 [SMILES: COC(=O)c1ccc(CN(C(=O)Oc2ccc([N+](=O)[O-])cc2)c2ccccn2)cc1]

Methyl 4-((pyridine-2-ylamino)methyl)benzoate (0.040 g, 0.16 mmol) was dissolved in dimethylformamide (3 mL), and then potassium carbonate (0.046 g, 0.33 mmol) was slowly added thereto. After that, 4-nitrophenyl chloroformate (0.037 g, 0.18 mmol) was added to a resulting mixture, then a temperature of the resulting mixture was slowly raised up to 50° C., and then the resulting mixture was stirred for two days at that temperature. After a reaction was completed, an ethyl acetate layer was washed with saturated ammonium chloride aqueous solution three times, then an organic layer was dried by means of sodium sulfate and filtered, and then a filtrate was concentrated under reduced pressure. A concentrate was purified via column chromatography (silicon dioxide; ethyl acetate/hexane=0-50%), such that a title compound (0.048 g, 71%) was obtained in a yellow oil form.

$^1$H NMR (400 MHz, CDCl$_3$) δ 8.49-8.48 (m, 1H), 8.24 (dd, 2H, J=7.0, 2.2 Hz), 8.17 (dd, 2H, J=7.2, 2.0 Hz), 8.00 (d, 2H, J=8.4 Hz), 7.78 (t, 1H, J=3.8 Hz), 7.44 (d, 2H, J=8.0 Hz), 6.91 (dd, 2H, J=7.3, 2.1 Hz), 5.39 (brs, 2H), 3.92 (s, 3H); MS (ESI) m/z 408 (M$^+$+H).

[Step 3] Synthesis of methyl 4-((N-(pyridine-2-yl)morpholine-4-carboxamido)methyl)benzoate

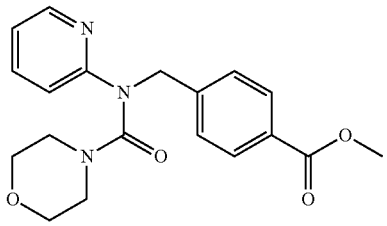 [SMILES: COC(=O)c1ccc(CN(C(=O)N2CCOCC2)c2ccccn2)cc1]

Methyl 4-((((4-nitrophenoxy)carbonyl)(pyridine-2-yl)amino)methyl)benzoate (0.040 g, 0.098 mmol) was dissolved in dimethylformamide (5 ml), and then potassium carbonate (0.040 g, 0.30 mmol) and morpholine (0.013 mL, 0.15 mmol) were slowly added thereto. After that, a temperature of a resulting mixture was slowly raised up to 80° C., and then the resulting mixture was stirred for three hours at that temperature. After a reaction was completed, the resulting mixture was washed with saturated ammonium chloride aqueous solution three times, then an organic layer was dried by means of sodium sulfate and filtered, and then a filtrate was concentrated under reduced pressure. A concentrate was purified via column chromatography (silicon dioxide; ethyl acetate/hexane=0-50%), such that a title compound (0.022 g, 63%) was obtained in a light yellow solid form.

$^1$H NMR (400 MHz, CDCl$_3$) δ 8.37-8.35 (m, 1H), 7.95 (d, 2H, J=8.4 Hz), 7.60-7.58 (m, 1H), 7.47 (d, 2H, J=8.4 Hz), 6.94-6.89 (m, 2H), 5.13 (s, 2H), 3.89 (s, 3H), 3.53-3.51 (m, 4H), 3.31-3.29 (m, 4H).

[Step 4] Synthesis of N-(4-(hydroxycarbamoyl)benzyl)-N-(pyridine-2-yl)morpholine-4-carboxamide

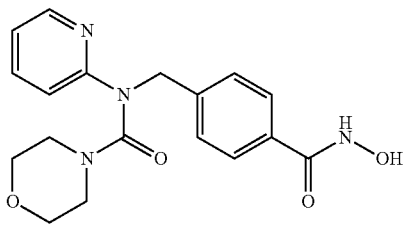 [SMILES: O=C(NO)c1ccc(CN(C(=O)N2CCOCC2)c2ccccn2)cc1]

Methyl 4-((N-(pyridine-2-yl)morpholine-4-carboxamido)methyl)benzoate (0.022 g, 0.062 mmol) was dissolved in MeOH (2 ml), and then hydroxylamine hydrochloric acid (0.022 g, 0.31 mmol) was slowly added thereto. After that, potassium hydroxide (0.035 g, 0.62 mmol) was inserted into a resulting mixture, then stirred at room temperature for ten minutes, and then hydroxylamine (50.0 wt % aqueous solution, 0.082 mL, 1.24 mmol) was inserted thereinto. After the resulting mixture was stirred at room temperature for a day, an organic solvent was concentrated under reduced pressure, then neutralized with the addition of 2N HCl, then washed with saturated sodium chloride aqueous solution three times, and then an organic layer was dried by means of anhydrous sodium sulfate and filtered, such that a title compound (0.007 g, 32%) was obtained in a white solid form.

$^1$H NMR (400 MHz, MeOD-d$_3$) δ 8.32 (d, 1H, J=3.6 Hz), 7.72 (t, 1H, J=6.6 Hz), 7.67 (d, 2H, J=8.2 Hz), 7.48 (d, 2H, J=8.2 Hz), 7.08-7.01 (m, 2H), 5.08 (s, 2H), 3.52 (t, 4H, J=4.8 Hz), 3.29 (t, 4H, J=4.8 Hz); MS (ESI) m/z 357 (M$^+$+H).

Preparation Example 3. Synthesis of compound 374 {N-(4-(hydroxycarbamoyl)benzyl)-N-(3-(trifluoromethyl)phenyl)morpholine-4-carboxamide}

[Step 1] Synthesis of methyl 4-((3-(trifluoromethyl)phenylamino)methyl)benzoate

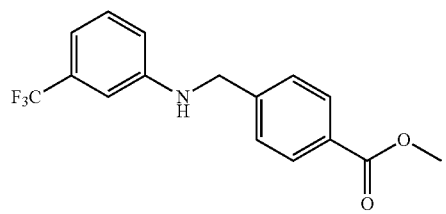 [SMILES: COC(=O)c1ccc(CNc2cccc(C(F)(F)F)c2)cc1]

3-(trifluoromethyl)benzeneamine (0.30 g, 1.84 mmol) and potassium carbonate (0.76 g, 5.53 mmol) were dissolved in dimethylformamide (DMF) (5 mL), and then methyl 4-(bromomethyl)benzoate (0.42 g, 1.84 mmol) was inserted thereinto. A resulting mixture was reacted at room temperature for a day and diluted with ethyl acetate. A reactant was washed with water and saturated sodium chloride aqueous solution, then dried by means of anhydrous magnesium sulfate and filtered, and then concentrated under reduced pressure. A residue was purified via column chromatography (silicon dioxide; ethyl acetate/hexane=20%), such that a title compound (0.37 g, 65%) was obtained.

$^1$H NMR (400 MHz, DMSO-d$_6$) δ 7.93 (d, 2H, J=8.3 Hz), 7.49 (d, 2H, J=8.3 Hz), 7.24 (t, 1H, J=7.9 Hz), 6.88-6.78 (m, 4H), 4.42 (d, 2H, J=6.1 Hz), 3.83 (s, 3H), MS (ESI) m/z 310 (M$^+$+H).

[Step 2] Synthesis of methyl 4-(((((4-nitrophenoxy)carbonyl)(3-(trifluoromethyl)phenyl)amino)methyl)benzoate

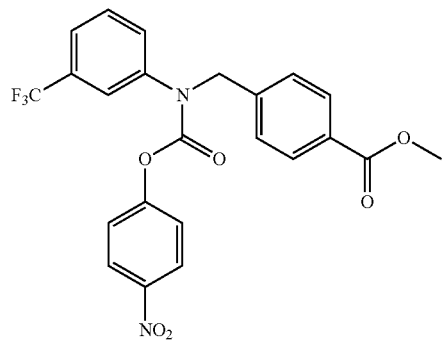 [SMILES: COC(=O)c1ccc(CN(C(=O)Oc2ccc([N+](=O)[O-])cc2)c2cccc(C(F)(F)F)c2)cc1]

Methyl 4-((3-(trifluoromethyl)phenylamino)methyl)benzoate (0.26 g, 0.82 mmol) and 4-nitrophenyl carbonochloridate (0.33 g, 1.65 mmol) were dissolved in acetonitrile (10 mL), and then potassium carbonate (0.34 g, 2.47 mmol) was inserted thereinto. A resulting mixture was reacted at room temperature for a day and diluted with ethyl acetate. A reactant was washed with saturated sodium chloride aqueous solution, then dried by means of anhydrous sodium sulfate and filtered, and then concentrated under reduced pressure. A residue was purified via column chromatography (silicon dioxide; ethyl acetate/hexane=20%), such that a title compound (0.35 g, 89%) was obtained in a colorless oil form.

$^1$H NMR (400 MHz, CDCl$_3$) δ 8.20 (d, 2H, J=10.2 Hz), 8.01 (d, 2H, J=7.8 Hz), 7.56-7.46 (m, 3H), 7.35 (d, 3H, J=8.0 Hz), 7.26 (d, 2H, J=8.1 Hz), 5.01 (bs, 2H), 3.90 (s, 3H).

[Step 3] Synthesis of methyl 4-((N-(3-(trifluoromethyl)phenyl)morpholine-4-carboxamido)methyl)benzoate

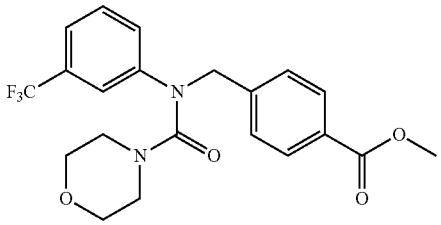 [SMILES: COC(=O)c1ccc(CN(C(=O)N2CCOCC2)c2cccc(C(F)(F)F)c2)cc1]

Methyl 4-((((4-nitrophenoxy)carbonyl)(3-(trifluoromethyl)phenyl)amino)methyl)benzoate (0.29 g, 0.60 mmol) was dissolved in dimethylformamide (10 ml), and then potassium carbonate (0.25 g, 1.81 mmol) and morpholine (0.05 mL, 0.60 mmol) were inserted thereinto. A resulting mixture was reacted at 60° C. for two days, and then diluted with saturated ammonium chloride solution. Extraction was performed by means of ethyl acetate, and then an extract was dried by means of anhydrous sodium sulfate and filtered, and then concentrated under reduced pressure. A residue was purified via column chromatography (silicon dioxide; ethyl acetate/hexane=50%), such that a title compound (0.15 g, 60%) was obtained.

$^1$H NMR (400 MHz, DMSO-d$_6$) δ 7.97 (d, 2H, J=8.2 Hz), 7.43-7.32 (m, 5H), 7.20 (d, 1H, J=8.0 Hz), 4.94 (s, 2H), 3.90 (s, 3H), 3.50 (t, 4H, J=4.8 Hz), 3.25 (t, 4H, J=4.8 Hz); MS (ESI) m/z 423 (M$^+$+H).

[Step 4] Synthesis of N-(4-(hydroxycarbamoyl)benzyl)-N-(3-(trifluoromethyl)phenyl)morpholine-4-carboxamide

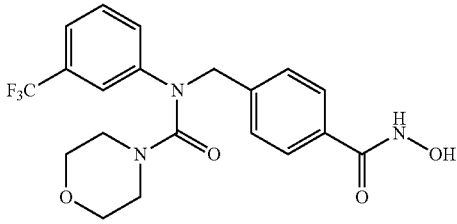 [SMILES: O=C(NO)c1ccc(CN(C(=O)N2CCOCC2)c2cccc(C(F)(F)F)c2)cc1]

Methyl 4-((N-(3-(trifluoromethyl)phenyl)morpholine-4-carboxamido)methyl)benzoate (0.15 g, 0.36 mmol) was dissolved in methanol (5 mL), then hydroxylamine aqueous solution (50 wt %, 1 mL) and potassium hydroxide (0.10 g, 1.81 mmol) were inserted thereinto, and then stirred overnight. After a reaction was completed, methanol was distilled under reduced pressure and removed, and then extraction was performed by means of ethyl acetate and water, and then worked up. A resulting extract was dried by means of anhydrous sodium sulfate and filtered, and then concentrated under reduced pressure. A residue was stirred in diethyl ether, and then a solid product was made, filtered and dried, such that a title compound (0.082 g, 54%) was obtained in a white solid form.

$^1$H NMR (400 MHz, MeOD-d$_3$) δ 11.14 (brs, 1H), 8.99 (brs, 1H), 7.85 (d, 2H, J=8.0 Hz), 7.66-7.27 (m, 6H), 4.94 (s, 2H), 3.41 (s, 2H), 3.15 (s, 2H). MS (ESI) m/z 424 (M$^+$+H).

Preparation Example 4. Synthesis of compound 416 {N-(2,4-difluorophenyl)-N-(4-(hydroxycarbamoyl)benzyl)-4-methylpiperazine-1-carboxamide}

[Step 1] Synthesis of methyl 4-((N-(2,4-difluorophenyl)-4-methylpiperazine-1-carboxamido)methyl)benzoate

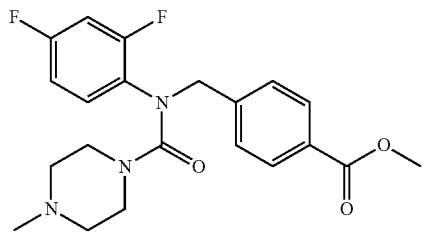

Methyl 4-(((2,4-difluorophenyl)((4-nitrophenoxy)carbonyl)amino)methyl)benzoate (0.50 g, 1.13 mmol) and 1-methylpiperazine (0.126 mL, 1.13 mmol) were dissolved in dimethylformamide (10 mL), and then heated and stirred at 60° C. for two days. Dimethylformamide was removed under reduced pressure, then water was poured into a resulting reaction mixture, and then extraction was performed by means of ethyl acetate. An organic layer was washed with saturated sodium chloride aqueous solution, then dehydrated by means of anhydrous magnesium sulfate, and then concentrated under reduced pressure. A residue was purified via column chromatography (silicon dioxide; methanol/dichloromethane=5%) and concentrated, such that a title compound (0.46 g, 101%) was obtained in a yellow oil form.

[Step 2] Synthesis of N-(2,4-difluorophenyl)-N-(4-(hydroxycarbamoyl)benzyl)-4-methylpiperazine-1-carboxamide

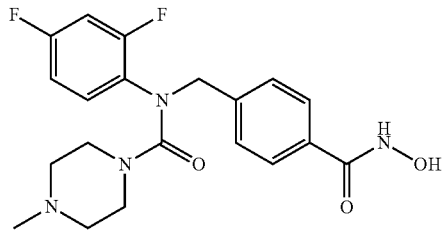 [SMILES: CN1CCN(C(=O)N(Cc2ccc(C(=O)NO)cc2)c2ccc(F)cc2F)CC1]

Methyl 4-((N-(2,4-difluorophenyl)-4-methylpiperazine-1-carboxamido)methyl)benzoate (0.22 g, 0.545 mmol) was dissolved in methanol (20 mL), then hydroxylamine hydrochloric acid (0.189 g, 2.73 mmol) and potassium hydroxide (0.306 g, 5.45 mmol) were added thereto and stirred, then hydroxylamine (50 wt % aqueous solution; 0.701 mL, 10.9 mmol) was added dropwise thereto, and then stirred at room temperature for three hours. After a reaction was completed, methanol was removed under reduced pressure, then water was poured into a resulting reaction mixture, and then extraction was performed by means of ethyl acetate. An organic layer was washed with saturated sodium chloride aqueous solution, then dehydrated by means of anhydrous magnesium sulfate, and then concentrated under reduced pressure. After that, a resulting concentrate was dissolved in dichloromethane, then hexane was added thereto, then a solid was precipitated, filtered and dried, such that a title compound (0.154 g, 70%) was obtained in a yellow solid form.

$^1$H NMR (400 MHz, MeOD-d$_3$) δ 7.65 (d, 2H, J=8.2 Hz), 7.40 (d, 2H, J=8.2 Hz), 7.26-7.25 (m, 1H), 7.04-6.96 (m, 2H), 4.79 (s, 2H), 3.25-3.23 (m, 4H), 2.24-2.21 (m, 7H); MS (ESI) m/z 405.1 (M$^+$+H).

Preparation Example 5. Synthesis of compound 461 {4-ethyl-N-(4-(hydroxycarbamoyl)benzyl)-N-(3-(trifluoromethyl)phenyl)piperazine-1-carboxamide}

[Step 1] Synthesis of methyl 4-((4-ethyl-N-(3-(trifluoromethyl)phenyl)piperazine-1-carboxamido)methyl)benzoate

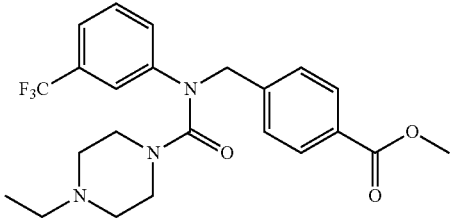 [SMILES: CCN1CCN(C(=O)N(Cc2ccc(C(=O)OC)cc2)c2cccc(C(F)(F)F)c2)CC1]

Methyl 4-((((4-nitrophenoxy)carbonyl)(3-(trifluoromethyl)phenyl)amino)methyl)benzoate (0.346 g, 0.73 mmol) was dissolved in dimethylformamide (10 ml), and then potassium carbonate (0.30 g, 2.19 mmol) and 1-ethylpiperazine (0.09 mL, 0.73 mmol) were inserted thereinto. A resulting mixture was reacted at 60° C. for a day, then diluted with ethyl acetate, and then washed with saturated ammonium chloride solution. The resulting mixture was dried by means of anhydrous magnesium sulfate and filtered, and then concentrated under reduced pressure. A residue was purified via column chromatography (silicon dioxide; ethyl acetate/hexane=50%), such that a title compound (0.15 g, 46%) was obtained.

[Step 2] Synthesis of 4-ethyl-N-(4-(hydroxycarbamoyl)benzyl)-N-(3-(trifluoromethyl)phenyl)piperazine-1-carboxamide

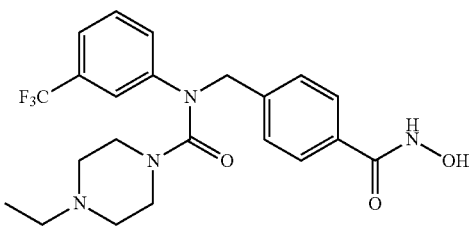 [SMILES: CCN1CCN(C(=O)N(Cc2ccc(C(=O)NO)cc2)c2cccc(C(F)(F)F)c2)CC1]

Methyl 4-((4-ethyl-N-(3-(trifluoromethyl)phenyl)piperazine-1-carboxamido)methyl)benzoate (0.15 g, 0.33 mmol) was dissolved in methanol (10 mL), then hydroxylamine (50 wt % aqueous solution, 0.20 mL) and potassium hydroxide (0.09 g, 1.67 mmol) were added thereinto, and then stirred overnight. After a reaction was completed, methanol was distilled under reduced pressure and removed, then extraction was performed by means of ethyl acetate and water, and then worked up. A resulting extract was dried by means of anhydrous magnesium sulfate and filtered, and then concentrated under reduced pressure. A residue was stirred in diethyl ether, and then a solid was made, filtered and dried, such that a title compound (0.09 g, 61%) was obtained in a yellow solid form.

$^1$H NMR (400 MHz, DMSO-d$_6$) δ 11.1 (brs, 1H), 7.65 (d, 2H, J=8.2 Hz), 7.51 (t, 1H, J=7.9 Hz), 7.41-7.36 (m, 5H), 4.92 (s, 2H), 3.17-3.14 (m, 4H), 2.25, 2.22 (ABq, 2H, J=12.4, 7.2 Hz), 2.18-2.15 (m, 4H), 0.92 (t, 3H, J=7.2 Hz); MS (ESI) m/z 451.1 (M$^+$+H).

Preparation Example 6. Synthesis of compound 476 {3,3-difluoro-N-(4-(hydroxycarbamoyl)benzyl)-N-(3-(trifluoromethyl)phenyl)azetidine-1-carboxamide}

[Step 1] Synthesis of methyl 4-((3,3-difluoro-N-(3-(trifluoromethyl)phenyl)azetidine-1-carboxamido)methyl)benzoate

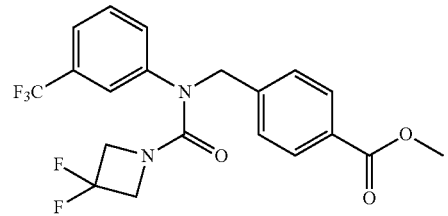 [SMILES: COC(=O)c1ccc(CN(C(=O)N2CC(F)(F)C2)c2cccc(C(F)(F)F)c2)cc1]

Methyl 4-((((4-nitrophenoxy)carbonyl)(3-(trifluoromethyl)phenyl)amino)methyl)benzoate (0.24 g, 0.51 mmol) was dissolved in dimethylformamide (5 ml), and then potassium carbonate (0.21 g, 1.52 mmol) and 3,3-difluoroazetidine hydrochloride (0.13 g, 1.10 mmol) were inserted thereinto. A resulting mixture was reacted at 60° C. for two days, and then diluted with saturated ammonium chloride solution. Extraction was performed by means of ethyl acetate, and then a resulting extract was dried by means of anhydrous sodium sulfate and filtered, and then concentrated under reduced pressure. A residue was purified via column chromatography (silicon dioxide; ethyl acetate/hexane=30%), such that a title compound (0.14 g, 63%) was obtained.

[Step 2] Synthesis of 3,3-difluoro-N-(4-(hydroxycarbamoyl)benzyl)-N-(3-(trifluoromethyl)phenyl)azetidine-1-carboxamide

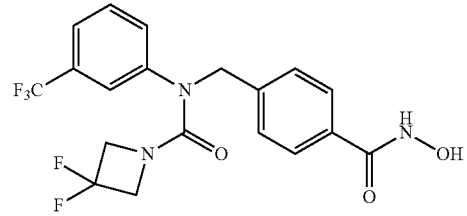 [SMILES: O=C(NO)c1ccc(CN(C(=O)N2CC(F)(F)C2)c2cccc(C(F)(F)F)c2)cc1]

Methyl 4-((3,3-difluoro-N-(3-(trifluoromethyl)phenyl)azetidine-1-carboxamido)methyl)benzoate (0.14 g, 0.32 mmol) was dissolved in methanol (10 mL), then hydroxylamine aqueous solution (50 wt %, 0.2 mL) and potassium hydroxide (0.09 g, 1.60 mmol) were inserted thereinto, and then stirred overnight. After a reaction was completed, methanol was distilled under reduced pressure and removed, and then extraction was performed by means of ethyl acetate and water, and then worked up. A resulting extract was dried by means of anhydrous sodium sulfate and filtered, and then concentrated under reduced pressure. A residue was stirred in diethyl ether, and then a solid product was made, filtered and dried, such that a title compound (0.072 g, 52%) was obtained in a white solid form.

Preparation Example 7. Synthesis of compound 500 {N-(3-(fluoromethyl)phenyl)-N-(4-(hydroxycarbamoyl)benzyl)morpholine-4-carboxamide}

[Step 1] Synthesis of methyl 4-((N-(3-(fluoromethyl)phenyl)morpholine-4-carboxamido)methyl)benzoate

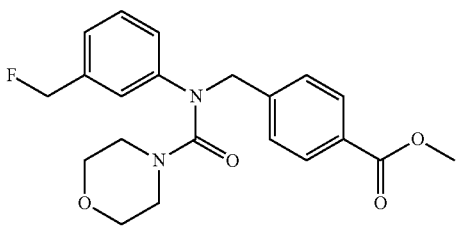 [SMILES: COC(=O)c1ccc(CN(C(=O)N2CCOCC2)c2cccc(CF)c2)cc1]

4-((N-(3-(hydroxymethyl)phenyl)morpholine-4-carboxamido)methyl)benzoic acid (1.25 g, 3.25 mmol) was dissolved in dichloromethane (20 mL), then diethylaminosulfur trifluoride (DAST, 0.424 mL, 3.58 mmol) was added thereto at 0° C., then stirred at the same temperature for one hour, then saturated sodium hydrogen carbonate aqueous solution was poured into a resulting reaction mixture, and then extraction was performed by means of dichloromethane. An organic layer was washed with saturated sodium chloride aqueous solution, then dehydrated by means of anhydrous magnesium sulfate, and then concentrated under reduced pressure. A residue was purified via column chromatography (silicon dioxide; ethyl acetate/hexane=30-50%) and concentrated, such that a title compound (0.617 g, 49%) was obtained in a colorless liquid form.

[Step 2] Synthesis of N-(3-(fluoromethyl)phenyl)-N-(4-(hydroxycarbamoyl)benzyl)morpholine-4-carboxamide

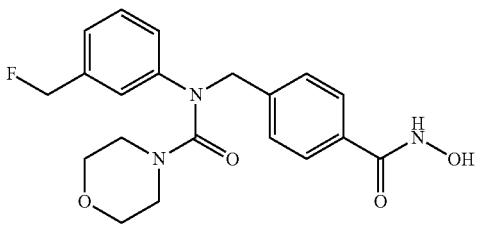 [SMILES: O=C(NO)c1ccc(CN(C(=O)N2CCOCC2)c2cccc(CF)c2)cc1]

Methyl 4-((N-(3-(fluoromethyl)phenyl)morpholine-4-carboxamido)methyl)benzoate (0.100 g, 0.259 mmol) was dissolved in methanol (10 mL), and then hydroxylamine (50.0 wt % aqueous solution, 1.11 mL, 18.1 mmol) was added thereto at room temperature. Then, potassium hydroxide (0.145 g, 2.59 mmol) was added to a resulting mixture and stirred at the same temperature for 30 minutes. After that, solvent was removed from a resulting reaction mixture under reduced pressure, then saturated sodium hydrogen carbonate aqueous solution was poured into a resulting concentrate, and then extraction was performed by means of ethyl acetate. An organic layer was washed with saturated sodium chloride aqueous solution, then dehydrated by means of anhydrous magnesium sulfate, and then concentrated under reduced pressure. Dichloromethane (5 mL) and hexane (30 mL) were inserted into a resulting concentrate and stirred, and then a precipitated solid was filtered and dried, such that a title compound (0.089 g, 89%) was obtained in a white solid form.

$^1$H NMR (400 MHz, DMSO-$d_6$) δ 11.12 (brs, 1H), 8.98 (brs, 1H), 7.64 (d, 2H, J=8.3 Hz), 7.36-7.32 (m, 3H), 7.20 (s, 1H), 7.15 (d, 1H, J=7.5 Hz), 7.09 (d, 1H, J=7.4 Hz), 5.36 (d, 2H, J=47.5 Hz), 4.87 (s, 2H), 3.39 (t, 4H, J=4.6 Hz), 3.13 (t, 4H, J=4.6 Hz). MS (ESI) m/z 388 (M$^+$+H).

Preparation Example 8. Synthesis of compound 530 {N-(3-fluorophenyl)-N-(4-(hydroxycarbamoyl)benzyl)morpholine-4-carboxamide}

[Step 1] Synthesis of methyl 4-((3-fluorophenylamino)methyl)benzoate

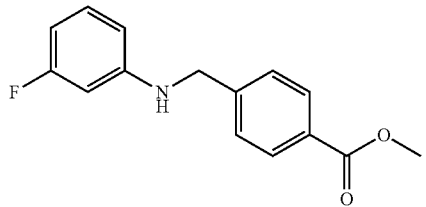 [SMILES: COC(=O)c1ccc(CNc2cccc(F)c2)cc1]

Methyl 4-formylbenzoate (1.47 g, 8.99 mmol) was dissolved in methanol (50 mL), and then 3-fluorobenzeneamine (1.0 g, 8.99 mmol) was inserted thereinto. A resulting mixture was reacted at room temperature for three hours, and then sodium cyanoborohydride (NaCNBH$_3$) (0.56 g, 8.99 mmol) and acetic acid (1.03 mL, 17.99 mmol) were inserted thereinto. After a reactant was reacted at room temperature for a day, reactant solvent was put under reduced pressure and removed, then saturated sodium hydrogen carbonate aqueous solution was poured thereinto, and then extraction was performed by means of ethyl acetate. An organic layer was dehydrated by means of anhydrous magnesium sulfate, and then concentrated under reduced pressure. A residue was purified via column chromatography (silicon dioxide; ethyl acetate/hexane=20%), such that a title compound (1.84 g, 79%) was obtained.

[Step 2] Synthesis of methyl 4-(((3-fluorophenyl)((4-nitrophenoxy)carbonyl)amino)methyl)benzoate

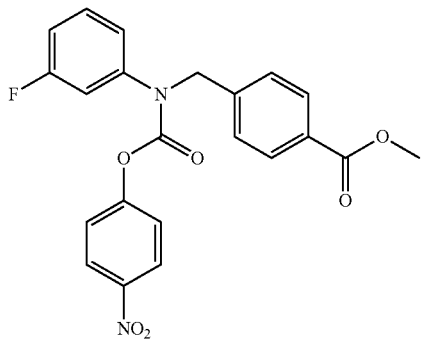 [SMILES: COC(=O)c1ccc(CN(C(=O)Oc2ccc([N+](=O)[O-])cc2)c2cccc(F)c2)cc1]

Methyl 4-((3-fluorophenylamino)methyl)benzoate (2.7 g, 10.4 mmol) and 4-nitrophenyl chloroformate (4.20 g, 20.8 mmol) were dissolved in acetonitrile (100 mL), and then potassium carbonate (4.32 g, 31.2 mmol) was inserted thereinto. A resulting mixture was reacted at room temperature for a day and diluted with ethyl acetate. A reactant was washed with saturated sodium chloride aqueous solution, then dried by means of anhydrous sodium sulfate and filtered, and then concentrated under reduced pressure. A residue was purified via column chromatography (silicon dioxide; ethyl acetate/hexane=20%), such that a title compound (2.65 g, 60%) was obtained in a colorless oil form.

[Step 3] Synthesis of methyl 4-((N-(3-fluorophenyl)morpholine-4-carboxamido)methyl)benzoate

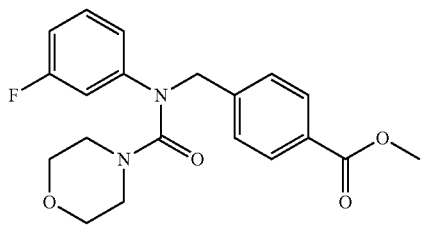 [SMILES: COC(=O)c1ccc(CN(C(=O)N2CCOCC2)c2cccc(F)c2)cc1]

Methyl 4-(((3-fluorophenyl)((4-nitrophenoxy)carbonyl)amino)methyl)benzoate (0.32 g, 0.75 mmol) was dissolved in dimethylformamide (5 ml), and then potassium carbonate (0.31 g, 2.24 mmol) and morpholine (0.13 mL, 1.49 mmol) were inserted thereinto. A resulting mixture was reacted at 60° C. for a day, and then diluted with saturated ammonium chloride solution. Extraction was performed by means of ethyl acetate, and then a resulting extract was dried by means of anhydrous sodium sulfate and filtered, and then concentrated under reduced pressure. A residue was purified via column chromatography (silicon dioxide; ethyl acetate/hexane=30%), such that a title compound (0.13 g, 45%) was obtained.

[Step 4] Synthesis of N-(3-fluorophenyl)-N-(4-(hydroxycarbamoyl)benzyl)morpholine-4-carboxamide

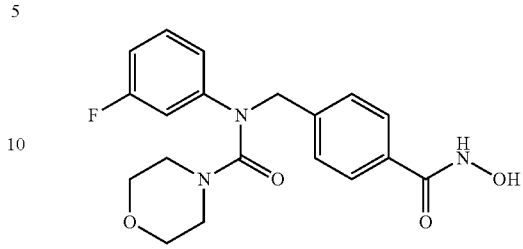

Methyl 4-((N-(3-fluorophenyl)morpholine-4-carboxamido)methyl)benzoate (0.108 g, 0.290 mmol) was dissolved in methanol (10 mL), and then hydroxylamine (50.0 wt % aqueous solution, 1.19 mL, 19.4 mmol) were added thereto at room temperature. Then, potassium hydroxide (0.156 g, 2.78 mmol) was added to a resulting mixture and stirred at the same temperature for 16 hours. After that, solvent was removed from a resulting reaction mixture under reduced pressure, then saturated sodium hydrogen carbonate aqueous solution was poured into a resulting concentrate, and then extraction was performed by means of ethyl acetate. An organic layer was washed with saturated sodium chloride aqueous solution, then dehydrated by means of anhydrous magnesium sulfate, and then concentrated under reduced pressure. A precipitated solid was filtered and dried, such that a title compound (0.062 g, 57%) was obtained in a white solid form.
$^1$H NMR (400 MHz, DMSO-$d_6$) δ 11.14 (brs, 1H), 8.99 (brs, 1H), 7.65 (d, 2H, J=7.0 Hz), 7.38-7.30 (m, 3H), 7.05-6.85 (m, 3H), 4.89 (s, 1H), 3.44-3.42 (m, 4H), 3.18-3.15 (m, 4H), 2.08 (s, 3H). MS (ESI) m/z 374 (M$^+$+H).

Preparation Example 9. Synthesis of compound 532 {N-(2-fluoro-4-(hydroxycarbamoyl)benzyl)-N-(3-(trifluoromethyl)phenyl)morpholine-4-carboxamide}

[ Step 1] Synthesis of 3-fluoro-4-(((3-(trifluoromethyl)phenyl)amino)methyl)benzonitrile

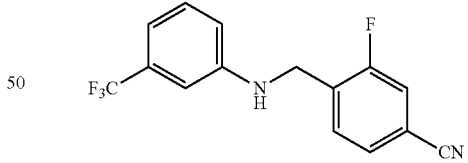

3-(trifluoromethyl)aniline (0.998 mL, 8.068 mmol) was dissolved in acetonitrile (60 mL), and then 4-(bromomethyl)-3-fluorobenzonitrile (2.072 g, 9.682 mmol) and DIPEA (2.143 mL, 12.102 mmol) were added thereto at room temperature, and then stirred at the same temperature for a day. After that, saturated sodium hydrogen carbonate aqueous solution was poured into a resulting reaction mixture, and then extraction was performed by means of ethyl acetate. An organic layer was washed with saturated sodium chloride aqueous solution, then dehydrated by means of anhydrous magnesium sulfate, and then concentrated under reduced pressure. A resulting concentrate was purified via column chromatography (silicon dioxide; ethyl acetate/ hexane=5-20%) and concentrated, such that a title compound (2.380 g, 64.4%) was obtained in a yellow liquid form.

[Step 2] Synthesis of 3-fluoro-4-(((3-(trifluoromethyl)phenyl)amino)methyl)benzoic acid

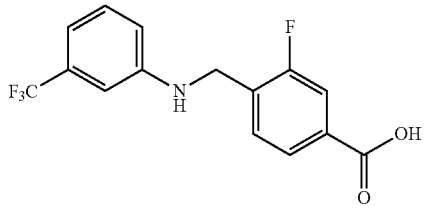 [SMILES: O=C(O)c1ccc(CNc2cccc(C(F)(F)F)c2)c(F)c1]

3-fluoro-4-(((3-(trifluoromethyl)phenyl)amino)methyl)benzonitrile (2.310 g, 7.850 mmol) and lithium hydroxide (3.294 g, 78.505 mmol) were mixed in methanol (40 mL)/H₂O (20 mL), then a resulting reaction mixture was heated under reflux for 16 hours, then cooled down to room temperature, and then the resulting reaction mixture was concentrated under reduced pressure. 2M hydrochloric acid aqueous solution was inserted into the resulting mixture to reach pH=1, and then a precipitated solid was filtered and dried, such that a title compound (1.700 g, 69.1%) was obtained in a white solid form.

[Step 3] Synthesis of methyl 3-fluoro-4-(((3-(trifluoromethyl)phenyl)amino)methyl)benzoate

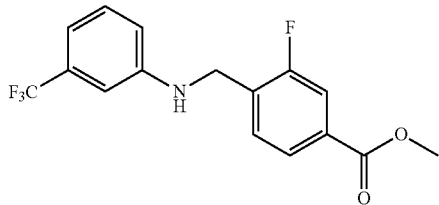 [SMILES: COC(=O)c1ccc(CNc2cccc(C(F)(F)F)c2)c(F)c1]

3-fluoro-4-(((3-(trifluoromethyl)phenyl)amino)methyl)benzoic acid (1.700 g, 5.427 mmol), methanol (4.402 mL, 108.540 mmol), EDC (2.081 g, 10.854 mmol), HOBt (1.467 g, 10.854 mmol) and DIPEA (2.883 mL, 16.281 mmol) were dissolved in tetrahydrofuran (50 mL) at room temperature, then a resulting reaction solution was stirred at the same temperature for 16 hours, then saturated sodium hydrogen carbonate aqueous solution was poured into a resulting reaction mixture, and then extraction was performed by means of ethyl acetate. An organic layer was washed with saturated sodium chloride aqueous solution, then dehydrated by means of anhydrous magnesium sulfate, and then concentrated under reduced pressure. A concentrate was purified via column chromatography (silicon dioxide; ethyl acetate/hexane=10-40%) and concentrated, such that a title compound (1.500 g, 84.5%) was obtained in a colorless liquid form.

[Step 4] Synthesis of methyl 3-fluoro-4-((((4-nitrophenoxy)carbonyl)(3-(trifluoromethyl)phenyl)amino)methyl)benzoate

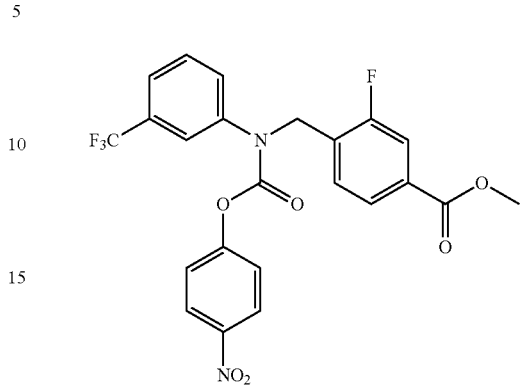

Methyl 3-fluoro-4-(((3-(trifluoromethyl)phenyl)amino)methyl)benzoate (1.500 g, 4.583 mmol), 4-nitrophenyl carbonochloridate (1.848 g, 9.167 mmol) and potassium carbonate (1.900 g, 13.750 mmol) were dissolved in acetonitrile (80 mL) at room temperature, then a resulting reaction solution was stirred at the same temperature for 16 hours, then saturated sodium hydrogen carbonate aqueous solution was poured into a resulting reaction mixture, and then extraction was performed by means of ethyl acetate. An organic layer was washed with saturated sodium chloride aqueous solution, then dehydrated by means of anhydrous magnesium sulfate, and then concentrated under reduced pressure. A resulting concentrate was purified via column chromatography (silicon dioxide; ethyl acetate/hexane=10-40%) and concentrated, such that a title compound (0.927 g, 41.1%) was obtained in a colorless liquid form.

[Step 5] Synthesis of methyl 3-fluoro-4-((N-(3-(trifluoromethyl)phenyl)morpholine-4-carboxamido)methyl)benzoate

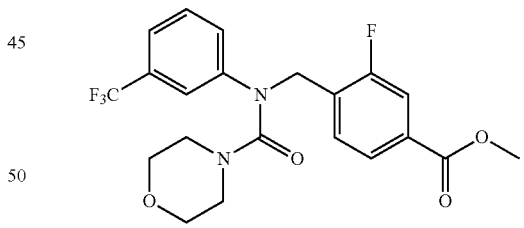

Methyl 3-fluoro-4-((((4-nitrophenoxy)carbonyl)(3-(trifluoromethyl)phenyl)amino)methyl)benzoate (0.129 g, 0.262 mmol), morpholine (0.046 mL, 0.524 mmol) and potassium carbonate (0.109 g, 0.786 mmol) were dissolved in N,N-dimethylformamide (5 mL) at 60° C., then a resulting reaction solution was stirred at the same temperature for two days, then saturated sodium hydrogen carbonate aqueous solution was poured into a resulting reaction mixture, and then extraction was performed by means of ethyl acetate. An organic layer was washed with saturated sodium chloride aqueous solution, then dehydrated by means of anhydrous magnesium sulfate, and then concentrated under reduced pressure. A resulting concentrate was purified via column chromatography (silicon dioxide; ethyl acetate/hexane=30-

60%) and concentrated, such that a title compound (0.094 g, 81.5%) was obtained in a colorless liquid form.

[Step 6] Synthesis of N-(2-fluoro-4-(hydroxycarbamoyl)benzyl)-N-(3-(trifluoromethyl)phenyl)morpholine-4-carboxamide

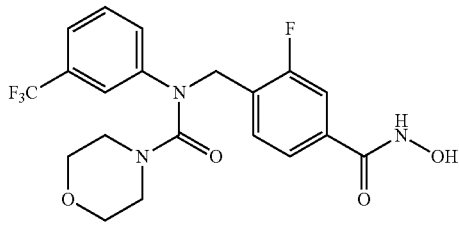 [SMILES: O=C(NO)c1ccc(CN(C(=O)N2CCOCC2)c2cccc(C(F)(F)F)c2)c(F)c1]

Methyl 3-fluoro-4-((N-(3-(trifluoromethyl)phenyl)morpholine-4-carboxamido)methyl)benzoate (0.094 g, 0.213 mmol) and hydroxylamine (50.0 wt % aqueous solution, 0.071 g, 2.134 mmol) were dissolved in methanol (5 mL), then potassium hydroxide (0.060 g, 1.067 mmol) was added thereto at room temperature, then stirred at the same temperature for two hours, and then a resulting reaction mixture was concentrated under reduced pressure. Diethyl ether (10 mL) was inserted into a resulting concentrate and stirred, and then a precipitated solid was filtered and dried, such that a compound 532 (0.068 g, 72.2%) was obtained in a bright yellow solid form.

$^1$H NMR (400 MHz, DMSO-d$_6$) δ 11.2 (brs, 1H), 9.13 (brs, 1H), 7.57-7.42 (m, 7H), 4.94 (s, 2H), 3.44-3.34 (m, 4H), 3.18-3.12 (m, 4H); MS (ESI) m/z 442.1 (M$^+$+H).

Preparation Example 10. Preparation of SLE Model Mouse

80 NZB/W F1 female mice (four weeks old) were purchased from Jackson Laboratory and maintained in an SPF breeding room with five mice per cage. Their weight and urine protein were measured at 24 weeks after birth (right before administration), and then all the animals except those having too much urine protein were divided into groups as shown in a table 2 below such that the urine protein and weight might be evenly distributed among the groups.

TABLE 2

| No. | Mouse group | Administered content | Administration | Population route (n) |
|---|---|---|---|---|
| 1 | C (negative control) | Vehicle | Intraperitoneal administration | 15 |
| 2 | P (positive control) | Methylprednisolone 5 mg/kg/day | Intraperitoneal administration | 15 |
| 3 | D (Experimental group 1) | Compound 374 10 mg/kg/day | Intraperitoneal administration | 15 |
| 4 | E (Experimental group 2) | Compound 374 30 mg/kg/day | Intraperitoneal administration | 15 |
| 5 | F (Experimental group 3) | Compound 374 50 mg/kg/day | Intraperitoneal administration | 15 |

Then, the mice were administered as described in the table 2 once a day for about 19 weeks from 24 weeks after birth to 42 weeks after birth.

The fresh urine of mice was collected before and after administration every two weeks, while blood collection was performed before and after administration every four weeks.

The serum was prepared by centrifugation of the collected blood and then kept at −70° C.

Example 1. Identification of Suppressive Effect on TNFα Secretion in Immune Cell Lines (In Vitro)

To identify the efficacy of the inventive compounds on suppressing a TNFα secretion in immune responses, suppression of TNFα production, which was achieved by a treatment with compounds 374, 461, 500, 530 and 532 according to the present invention in LPS-stimulated human monocyte cell lines (THP-1), was quantified by means of an enzyme immuno-assay (ELISA).

Specifically, the THP-1 cell lines (ATCC) were cultured in an RPMI-1640 medium comprising 10% FBS. The cell lines were divided into a 24 well plate at a ratio of 1×10$^5$ cells per well, then treated with 100 ng/mL PMA (phorbol 12-myristate 13-acetate) for 24 hours, and then differentiated into macrophage. Then, the culture medium was replaced with a new one, then treated with a test drug for 24 hours, and then treated again with 10 ng/mL LPS (E. Coli, O55:B5) for four hours for stimulation. After that, supernatant was taken and used to measure the amount of TNFα secreted from the cells by means of a Human TNFα Instant ELISA kit (eBioscience, BMS223INST) according to a protocol provided by a manufacturer.

As a result, it was shown that a level of TNFα secretion was decreased in all experimental groups in comparison with a control group, in which an inflammatory response was induced by means of the LPS. In FIG. 1, the compounds denoted as SM374, SM461, SM500, SM530 and SM532 are compounds 374, 461, 500, 530 and 532, respectively. In particular, in case of the compounds 374, 461 and 500, the level of TNFα secretion was remarkably decreased down to a level at which no inflammatory response was induced by means of the LPS at both 100 nM and 300 nM concentrations. Also, in case of increasing a concentration of compound treatment from 100 nM to 300 nM in the compounds 530 and 532, the level of TNFα secretion was drastically decreased (FIG. 1).

The experimental results above show that the compound according to the present invention very effectively suppresses the secretion of TNFα, i.e., an inflammatory response factor, which is representatively increased in lupus, thus effectively suppressing the inflammatory responses caused in lupus.

Example 2. Identification of Suppressive Effect on Reactive T Cells Proliferation (In Vitro)

To identify the efficacy of the inventive compounds on suppressing the proliferation of reactive T cells in immune responses, compounds 255, 280, 374, 416 and 476 according to the present invention were cultured together with reactive T cells and regulatory T cells in LPS-stimulated human monocyte cell lines (THP-1), and then the suppressive efficacy of regulatory T cells was measured.

Specifically, a six-week old C57BL6 male mice were supplied from Central Lab Animal Inc., then acclimated for one week, and then used in an experiment. A spleen was isolated from the mouse, and then treated with collagenase D (Roche, 11088866001), such that splenocytes were isolated therefrom. Treg (CD4+CD25−) and Teff (CD4+CD25+) were isolated by means of a CD4+CD25+ regulatory T cell isolation kit (Miltenyi Biotec, 130-091-041) according to a protocol provided by a manufacturer. Teff cells were cultured at 37° C. for ten minutes by means of eFluor®670 (Cell proliferation Dye eFluor®670, eBioscience), such that cell membranes were stained. Teff and Treg were divided into a 96 well plate at a ratio of 2:1, and then T cells were activated for three days by means of an anti-CD3E and anti-CD28 mAb magnetic bead (T cell activation/expansion kit, Miltenyi Biotec, 130-093627), such that Treg suppression assay was performed. A test drug was simultaneously treated for three days, during which the assay was performed.

The divided amount of eFluor®670 labeled on the Teff cell membranes was measured, such that a degree of proliferation of T cells was evaluated accordingly. An eFluor®670-dilution plot was measured by means of a flow cytometer (FACS LSR Fortessa, BD bioscience). The suppressive ability on T cells proliferation was calculated by means of a following equation.

$$\text{Relative suppression} = \frac{\% \text{ Division}(T_{eff} \text{only}) - \% \text{ Division(Drug)}}{\% \text{ Division}(T_{eff} \text{only}) - \% \text{ Division(vehicle)}}$$

Figure 2:
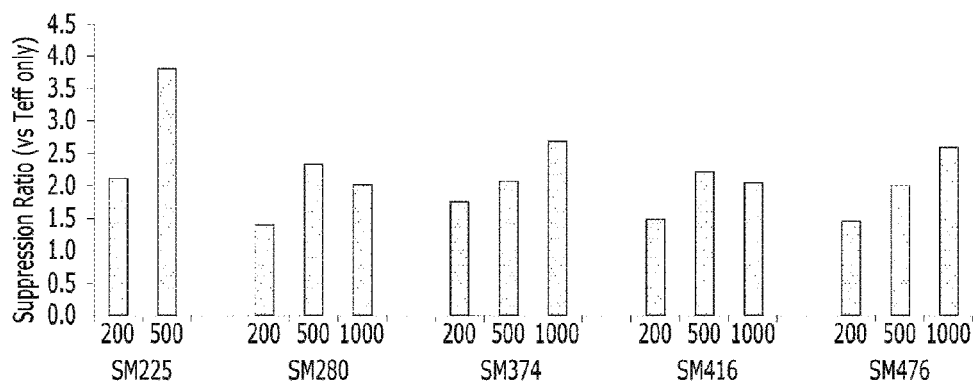
FIG. 2 shows results of identifying an effect of the inventive pharmaceutical composition on suppressing a proliferation of reactive T cells.

As a result, it was shown that the proliferation of the reactive T cells was suppressed in all the experimental groups. In FIG. 2, the compounds denoted as SM255, SM280, SM374, SM416, SM476 are compounds 255, 280, 374, 416, 476, respectively. The compounds according to the present invention used in the experiment showed a suppression ratio of reactive T cells proliferation, which exceeded maximum two-fold, when treated at 200 nM, and also showed a remarkable effect of suppressing T cells proliferation, which reached maximum four-fold, when treated at 500 nM (FIG. 2).

The experimental results above show that the compounds according to the present invention effectively suppresses the differentiation of the reactive T cells, which were excessively activated in lupus.

Example 3. Identification of Regulatory Effect of Regulatory T Cells Function (In Vitro)

To identify if the compounds according to the present invention regulate a function of regulatory T cells in immune responses, compounds 255, 280, 374, 416 and 476 were treated, and then an expression level of an immune checkpoint receptor CTLA4 (cytotoxic T-lymphocyte-associated protein 4) in the regulatory T cells was measured by means of flow cytometry.

Specifically, a six-week old C57BL6 male mice were supplied from Central Lab Animal Inc., then acclimated for one week, and then used in an experiment. A spleen was isolated from the mouse, and then treated with collagenase D (Roche, 11088866001), such that splenocytes were isolated therefrom. CD4+CD25− T cells were isolated by means of a CD4+CD25+ regulatory T cell isolation kit (Miltenyi Biotec, 130-091-041), and then CD4+CD25− T cells (at a ratio of $5 \times 10^5$ cells/well) were treated with an anti-CD3c/anti-CD28 mAb bead (T cell activation/expansion kit, Miltenyi Biotec, 130-093627) and a mouse recombinant TGF-$\beta_2$ for six days, such that they were differentiated into iTreg. A test drug was simultaneously treated for six days, during which the cells were differentiated into iTreg. After that, the cells were incubated by means of anti-CD$^4$/anti-CD25 mAb (eBioscience, 25-0042-82, 17-0251-82) at 4° C. for 20 minutes, and then labeling was performed. For intracytoplasmic staining, permeabilization was performed by means of Fix/permeabilization buffer (eBioscience, 00-5523-00), then labeling was performed by means of anti-FOXP3-Alexafluor488 (eBioscience, 53-5773-82) and anti-CTLA4-PE (eBioscience, 12-1522-82), and then flow cytometry was performed by means of FACS LSR Fortessa (BD bioscience).

Figure 3:
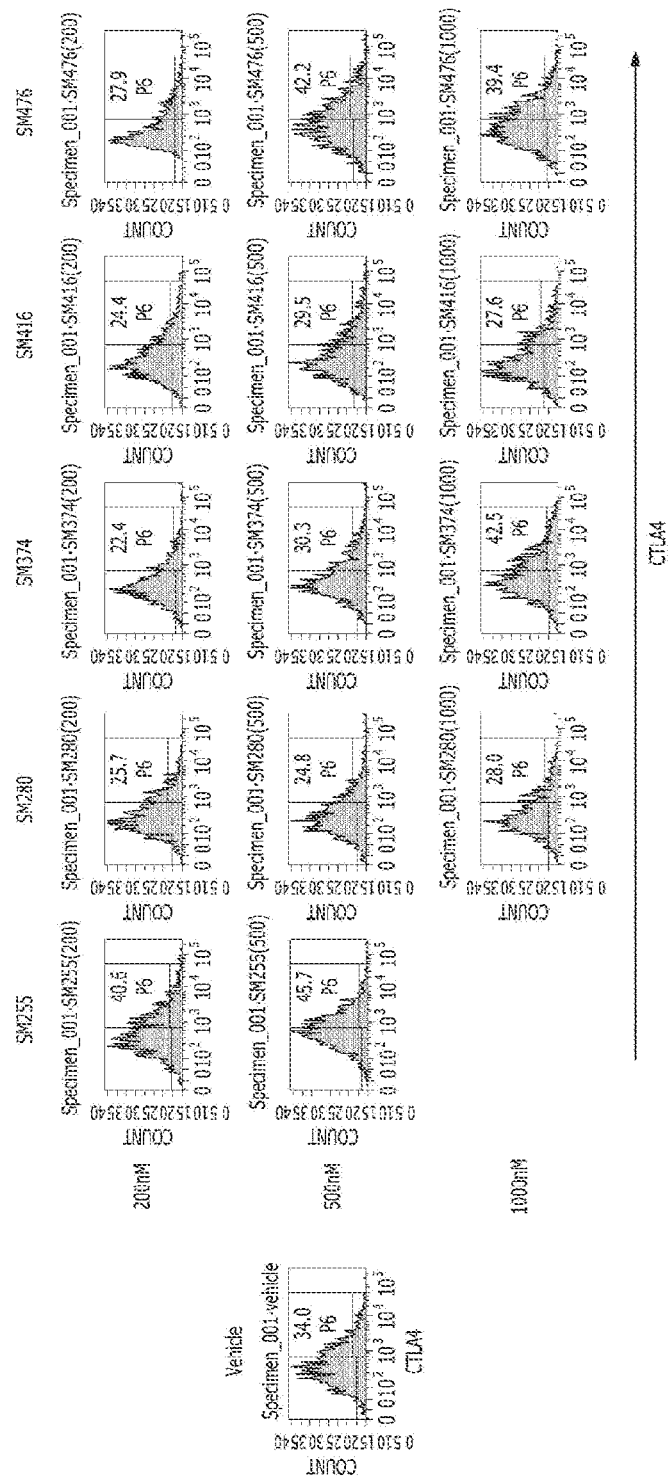
FIG. 3 shows results of identifying an effect of the inventive pharmaceutical composition on adjusting a function of regulatory T cells.

As a result, it was identified that a level of CTLA4 expression in the T cells was increased after treated with the compounds according to the present invention. In FIG. 3, the compounds denoted as SM255, SM280, SM374, SM416, SM476 are compounds 255, 280, 374, 416, 476, respectively. In particular, in case of compounds 255, 374 and 476, it was shown that the CTLA4 expression in 40% or more of the T cells was increased at a concentration of 500 nM or more. The compound 255 showed severe cytotoxicity when treated at 1000 nM, such that data analysis was not performed (FIG. 3).

The experimental results above show that the compounds according to the present invention improve a function of the regulatory T cells, such that an excessive activity of the reactive T cells caused in lupus might be effectively regulated.

Example 4. Weight Recovery Effect in Animal Model

Figure 4:
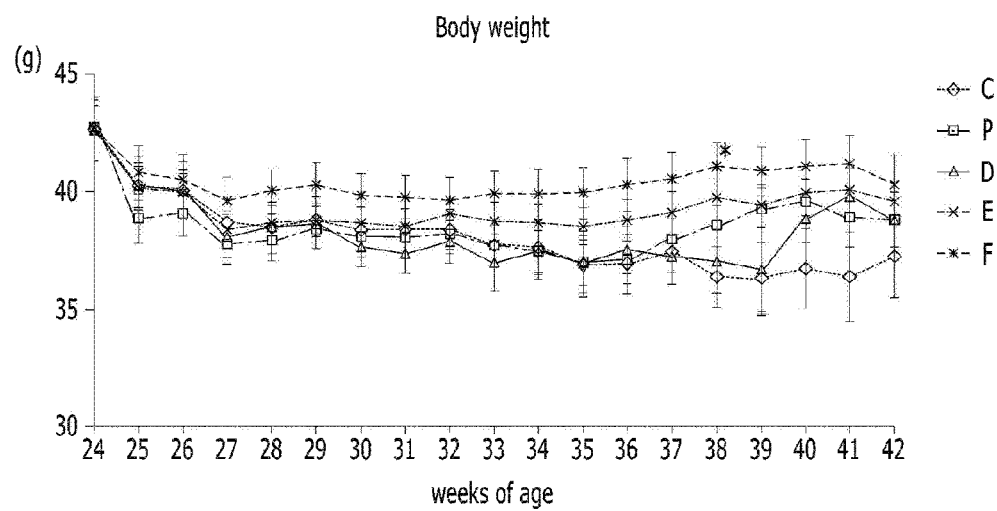
FIG. 4 shows an effect of the inventive pharmaceutical composition on recovering from a weight loss symptom in a disease animal model.

As a result of identifying a change in mouse weights, the weights showed an overall pattern of decrease after administration for the first four weeks (thought to be an action caused by solvent composed of ethanol+Kolliphor+saline), but a more salient weight recovery effect occurred in a positive control group than in a negative control group after 36 weeks old. In case of experimental groups, the weight in a 10 mg/kg dosed group was recovered to the same level as that of the positive control group from about 40 weeks, while a more excellent weight recovery effect was shown in 30 and 50 mg/kg dosed groups than in the positive control group (FIG. 4).

Example 5. Effect of Improving Survival Rate in Animal Model

An NZB/W F1 female mouse is used as a human SLE disease model. If not treated at all, it is known that this model falls dead all after 12 months or so (about 52 weeks old) due to immune-complex glomerulonephritis.

To identify if the pharmaceutical composition according to the present invention shows an effect of improving a survival rate in the SLE animal model, the survival rate of the NZB/W F1 female mice was measured every day for the whole experiment period from 24 weeks after birth to 42 weeks after birth.

Figure 5:
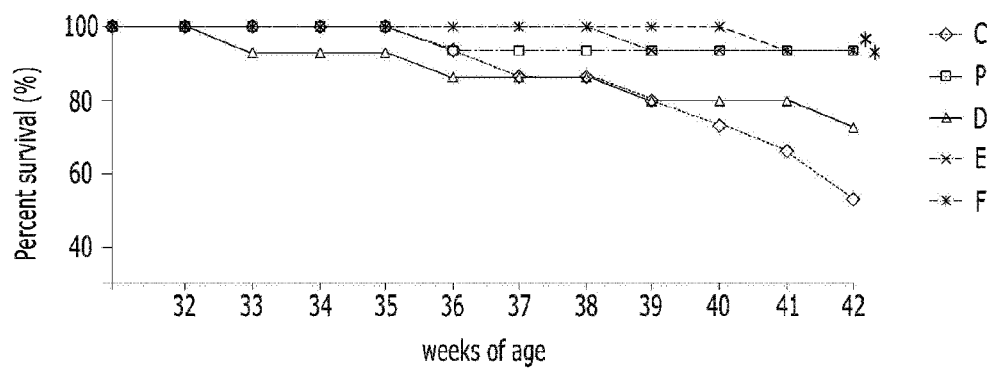
FIG. 5 shows an effect of the inventive pharmaceutical composition on improving a survival rate in the disease animal model.

As a result, there was no change in the survival rate in all the groups before 32 weeks or so after birth. In case of the negative control group without any drug treatment, the survival rate of mice was drastically decreased after 35 weeks after birth, such that 7 out of 15 mice fell dead at 42 weeks after birth (the survival rate of about 53.3%). On the contrary, both of the positive control group and the experimental groups tended to show better recovery pattern of the survival rate pattern of the survival rate than in the negative control group. In particular, 4 out of 15 mice (the survival rate of about 73.3%) fell dead at 42 weeks after birth in a 10 mg/kg dosed group, and surprisingly only one mouse (the survival rate of about 93.3%) fell dead in 30 mg/kg and 50 mg/kg dosed groups, thus it was identified that the pharmaceutical composition according to the present invention showed a remarkably excellent effect of improving the survival rate in the SLE animal model (FIG. 5).

Example 6. Proteinuria-Reducing Effect in Animal Model

To identify if the pharmaceutical composition according to the present invention shows a therapeutic effect on the production of proteinuria, i.e., a representative symptom of the SLE disease, the mouse's urine was collected every two weeks, and then UP/C (ratio of urine protein:creatine) was measured by means of a commassie brilliant blue (CBB) method. A urine creatinine concentration was obtained by diluting the urine 100-fold, then measuring the concentration thereof by means of a serum chemistry analyzer (Dri-CHEM 3000 colorimetric analyzer, Fujifilm), and then calibrating the measured value using a dilution factor.

Figure 6:
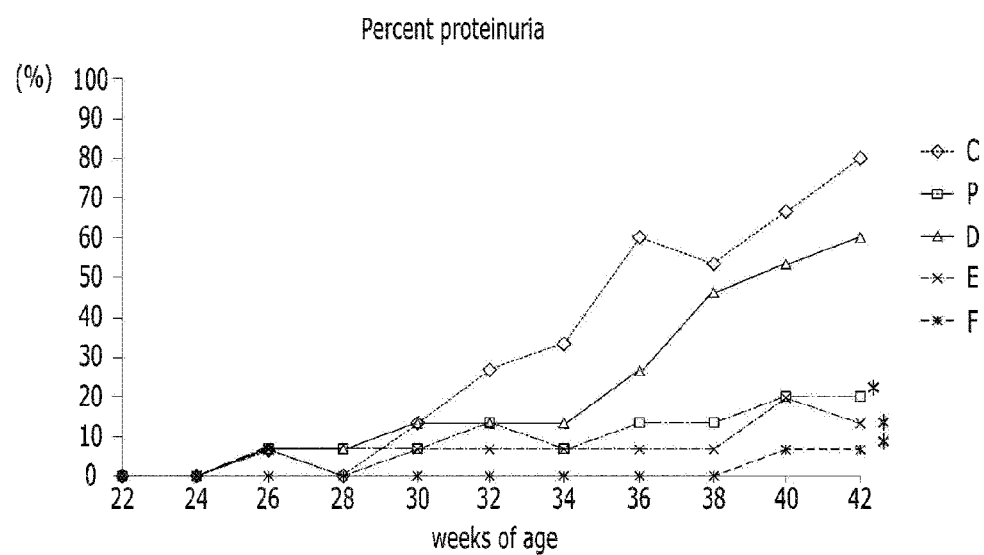
FIG. 6 shows an effect of the inventive pharmaceutical composition on reducing an incidence rate of proteinuria in the disease animal model.

As a result, it was identified that an incidence rate of severe proteinuria of 300 mg/dl or more was drastically increased with aging from 24 to 42 week after birth in the negative control group, while a problem with such incidence rate of severe proteinuria was remarkably improved in the experimental groups. In particular, the incidence rate of severe proteinuria of 300 mg/dl or more at 42 weeks old was 80% in the negative control group, while such incidence rate was 20% in the positive control group. Even it was also 60%, 6.7% and 0% in 10, 30 and 50 mg/kg dosed groups, respectively, which resulted in a remarkably excellent effect of reducing proteinuria (FIG. 6).

Figure 7:
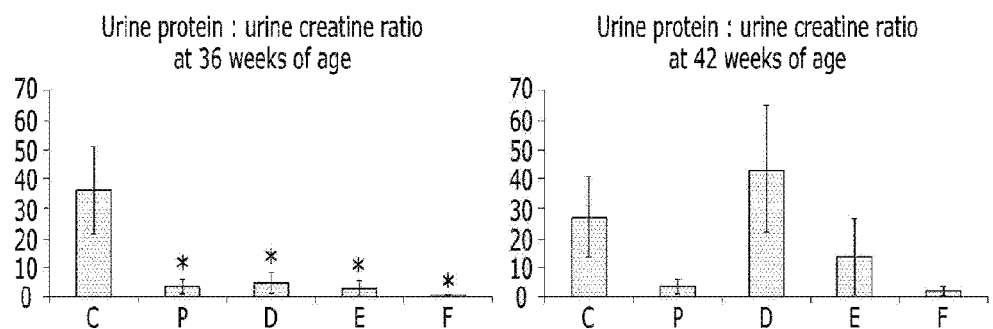
FIG. 7 shows an effect of the inventive pharmaceutical composition on reducing a UP/C value in the disease animal model.

Meanwhile, the UP/C of a 36-week old mouse was remarkably decreased in all the experimental groups. Even in case of a 42-week old mouse, it was identified that an UP/C value was decreased more in all the experimental groups except the 10 mg/kg dosed group than in the negative control group (FIG. 7).

Example 7. Effect of Reducing Serum Concentration of Anti-dsDNA Antibodies in Animal Model To identify if the pharmaceutical composition according to the present invention may reduce an increased concentration of anti-dsDNA antibodies shown in the SLE model animal, a concentration of anti-dsDNA antibodies in mouse serum was measured by means of a mouse anti-dsDNA ELISA (enzyme-linked immunosorbent assay) kit (Shibayagi).

Figure 8:
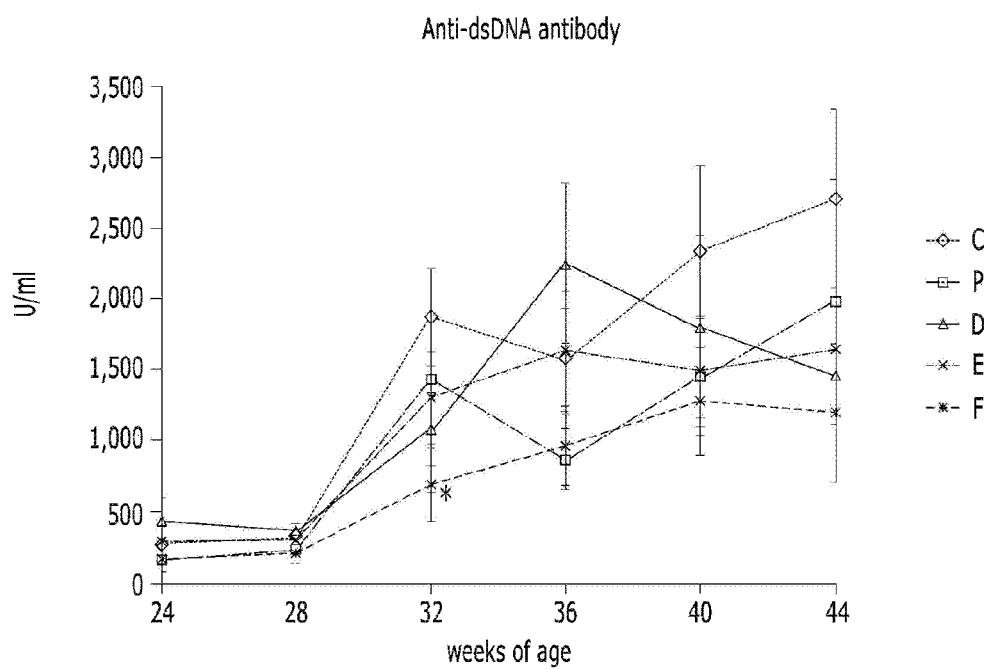
FIG. 8 shows an effect of the inventive pharmaceutical composition on reducing a serum concentration of anti-dsDNA antibodies in the disease animal model.

As a result, the serum concentration of anti-dsDNA antibodies after 28 week after birth tended to decrease more in all the experimental groups than in the negative control group. In particular, in case of the 50 mg/kg dosed group, it was identified that the serum concentration of anti-dsDNA antibodies was more remarkably decreased by more than maximum two-fold than the negative control group (FIG. 8).

Example 8. Effect of Reducing BUN and Serum Creatinine Concentrations in Animal Model To evaluate a kidney function of the SLE model mouse, BUN and creatine concentrations were measured from a mouse serum collected every month (at 24, 28, 32, 36 and 40 weeks old and during autopsy) by means of a Dri-CHEM 3000 colorimetric analyzer (Fuji film).

Figure 9:
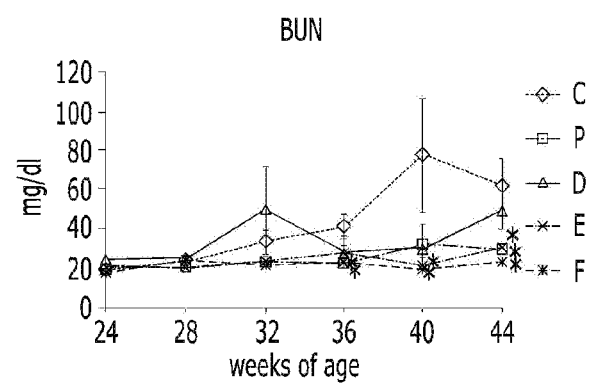
FIG. 9 shows an effect of the inventive pharmaceutical composition on reducing a serum concentration of BUN and creatine in the disease animal model.
Figure 9:
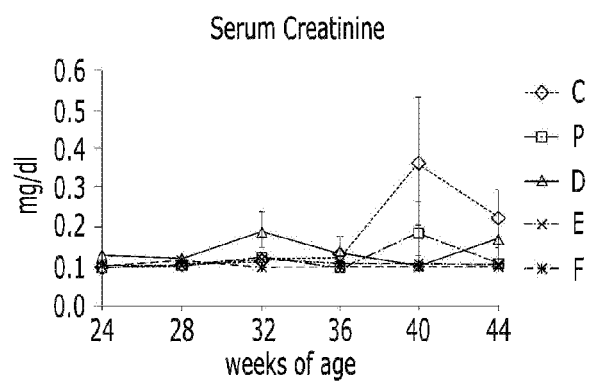

As a result, it was identified that the BUN and serum creatine concentrations were decreased in the experimental groups in comparison with the control groups, in particular it was also identified that there was a remarkably excellent effect of reducing the BUN and serum creatine concentrations at 40 weeks old (FIG. 9).

Example 9. Renal histological change in animal model

To identify an effect of the inventive pharmaceutical composition on kidney in the SLE disease model, a histopathological evaluation was performed.

First of all, a half of a left kidney of a mouse collected during the autopsy was fixed with 10% neutral buffered formalin and prepared as a paraffin block. Then, a histopathological evaluation was performed by means of hematoxylin and eosin staining (H&E, BBC Biochemical, Mount Vernon, Wash., USA), periodic acid-schiff staining (PAS, BBC Biochemical) and Masson's trichrome staining (BBC Biochemical).

Figure 10:
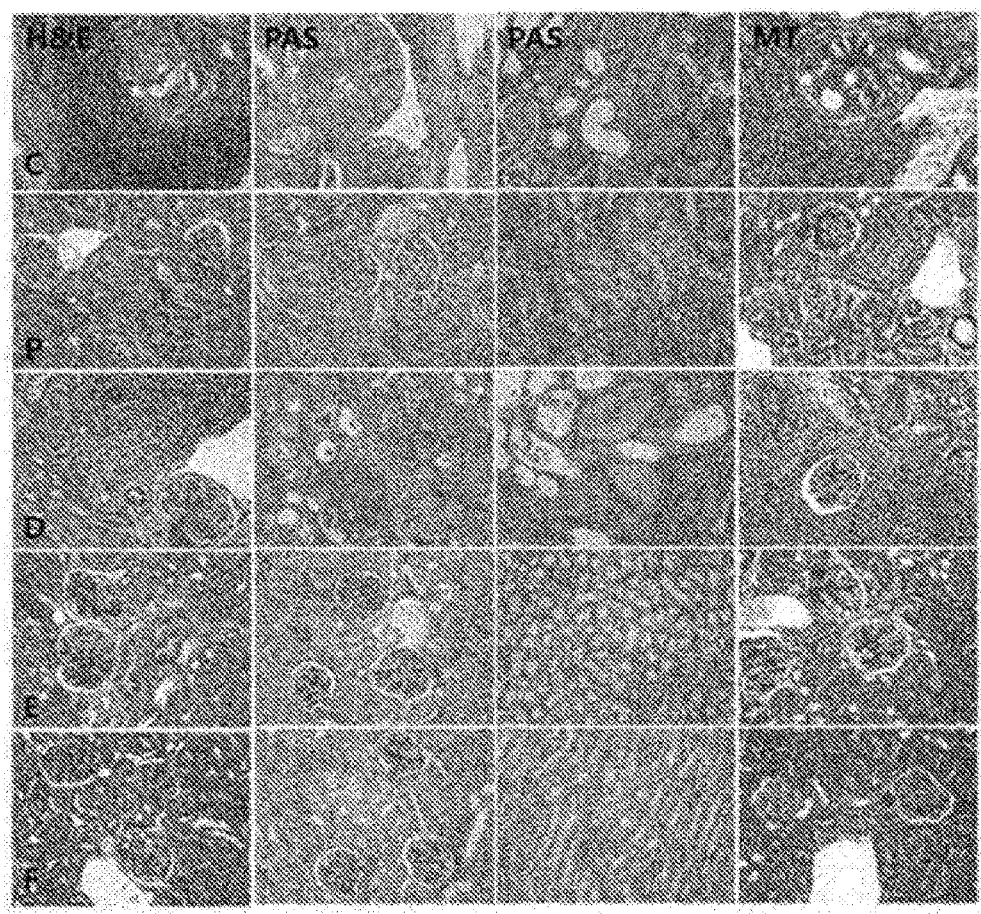
FIG. 10 shows a picture of stained kidney tissues in the disease animal model.

As a result, a finding about the infiltration of a number of inflammatory cells and mesangial proliferation was observed in the negative control group. During PAS staining, many expanded tubules and casts in the tubules were observed. During massion trichrome staining, fibrosis pattern was more prominent (FIG. 10).

Figure 11:
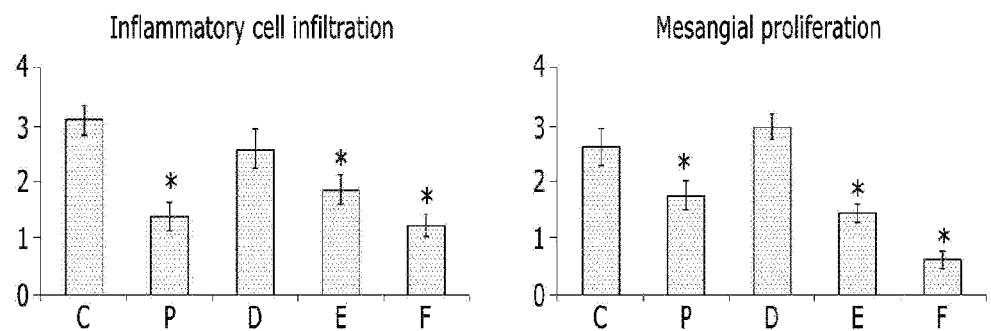
FIG. 11 shows an effect of the inventive pharmaceutical composition on renal histological changes in the disease animal model.

Then, when giving marks 0-4 (0: no infiltration, 4: severe infiltration) according to a degree of infiltration of inflammatory cells, the degree of infiltration of inflammatory cells was decreased in a mouse kidney of the experimental groups, in particular, it was identified that there was a remarkably excellent effect of reducing the infiltration of inflammatory cells in the 30 and 50 mg/kg dosed groups (FIG. 11).

Example 10. Identification of Effect of Reducing IgG and C3 Depositions in Kidney in Animal Model To identify a therapeutic effect of the inventive pharmaceutical composition on kidney in the SLE disease model, a degree of IgG and C3 depositions in glomerulus was measured.

With regard to a remaining half of the left kidney collected during the autopsy performed in Example 9, a frozen tissue block was prepared for a frozen section by means of an OCT compound, and then IgG and C3 fluorescence immunostaining was performed by means of a method known in the technical field to which the present invention pertains.

Specifically, the frozen tissue was sectioned in a thickness of 4 μm, then fixed in cold acetone for five minutes, and then washed in phosphate buffered saline (PBS) twice for five minutes. To get rid of a non-specific reaction, a resulting tissue was blocked by means of the PBS solution with the addition of 1% bovine serum albumin and 0.05% tween-20 for 30 minutes, and then reacted at room temperature for one hour by means of FITC-conjugated goat anti-mouse IgG antibodies (1:200, AP308F, Merck Millipore) or FITC-conjugated goat anti-mouse C3 antibodies (1:100, Cappel 55500, MP Bio). After that, the resulting tissue was washed with the PBS for five minutes three times, then covered with a cover glass by means of a mounting medium including DAPI, and then observed by means of a confocal laser scanning microscopy (LSM 700, ZEISS).

Figure 12:
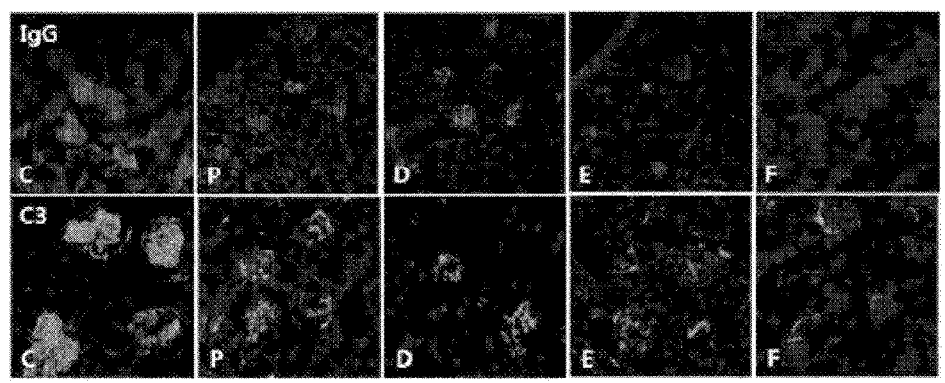
FIG. 12 shows an effect of the inventive pharmaceutical composition on reducing IgG and C3 depositions in kidney in the disease animal model.
Figure 12:
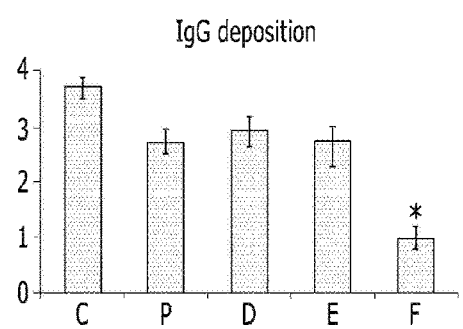
Figure 12:
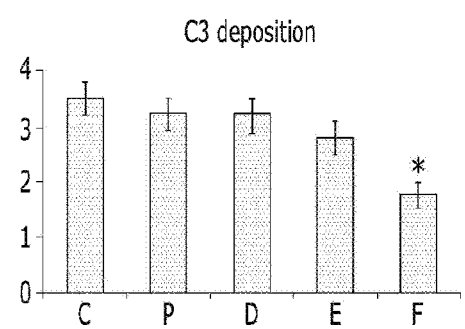

As a result, a level of IgG and C3 depositions was decreased in the experimental groups, in particular it was identified that the level of such depositions was remarkably decreased in the 50 mg/kg dosed group (FIG. 12).

Example 11. Serum Cytokine Concentration in Animal Model

To analyze an effect of the inventive pharmaceutical composition on a change in a serum cytokine level in the SLE disease mouse, a level of GM-CSF, IFN-γ, IL-1α, IL-1β, IL-10, IL-12(p70), IL-15, IL-17a, IL-2, IL-4, IL-6, TNF-α, TGF-0, IL-22 and IL-23 in serum was measured by means of a Mouse cytokine Milliplex MAP kit (Merck Millipore), wherein the results thereof were shown in a table 3.

TABLE 3

| pg/ml | C (n = 8) | P (n = 13) | D (n =10) | E (n = 14) | F (n = 14) |
|---|---|---|---|---|---|
| GM-CSF | 8.61 ± 5.84 | ND | 2.65 ± 2.65 | 5.32 ± 4.06 | 1.89 ± 1.89 |
| IFN-γ | 5.86 ± 4.42 | 0.07 ± 0.07 | 1.06 ± 1.06 | 6.60 ± 4.07 | 2.07 ± 1.44 |
| IL-10† | 1878.37 ± 1805.81 | 18.41 ± 3.60 | 25.00 ± 8.01 | 56.55 ± 39.16 | 8.31 ± 3.78* |
| IL-12(70)† | 2514.76 ± 2439.05 | 1.04 ± 1.04 | 1.94 ± 1.17 | 74.50 ± 63.63 | 15.62 ± 12.09 |
| IL-15† | 255.59 ± 119.34 | 45.25 ± 4.14* | 184.36 ± 88.58 | 162.41 ± 53.62 | 26.24 ± 7.68* |
| IL17† | 581.77 ± 558.60 | 3.59 ± 0.48* | 10.40 ± 3.86 | 21.14 ± 14.59 | 4.82 ± 1.91* |
| IL-1α | 289.98 ± 119.34 | 666.21 ± 146.22 | 371.96 ± 82.72 | 458.40 ± 90.79 | 629.16 ± 128.47 |
| IL-1β | 1.58 ± 1.11 | 0.65 ± 0.65 | 1.27 ± 0.65 | 74.66 ± 70.56 | 3.86 ± 2.09 |
| IL-2 | 6.96 ± 5.27 | 0.09 ± 0.09 | 1.91 ± 1.77 | 9.32 ± 4.75 | 4.09 ± 2.63 |
| IL-4 | 51.52 ± 45.05 | 1.49 ± 0.06 | 1.74 ± 0.19 | 8.60 ± 6.80 | 3.70 ± 1.73 |
| IL-6 | 1275.32 ± 1253.30 | 3.36 ± 0.92 | 7.21 ± 2.34 | 21.23 ± 13.62 | 5.69 ± 2.39 |
| TNF-α† | 7.33 ± 1.42 | 1.57 ± 0.57* | 7.91 ± 2.67 | 16.25 ± 13.46 | 1.24 ± 0.69* |
| TGF-β | 51494.48 ± 8345.48 | 66007.78 ± 5207.83 | 73356.45 ± 7258.05 | 58807.36 ± 6685.72 | 73110.92 ± 0.32* |
| IL22 | 31.00 ± 16.42 | 17.68 ± 4.49 | 27.05 ± 9.95 | 13.00 ± 4.40 | 6.37 ± 1.49* |
| IL-23 | 126.59 ± 68.41 | 22.31 ± 17.13 | 1.96 ± 1.96 | 100.56 ± 100.56 | 41.34 ± 41.34 |

Data obtained from groups were compared using a Kruskal-Wallis (†p<0.05) *p<0.05 versus C group (Mann-Whitney U-test)

Figure 13:
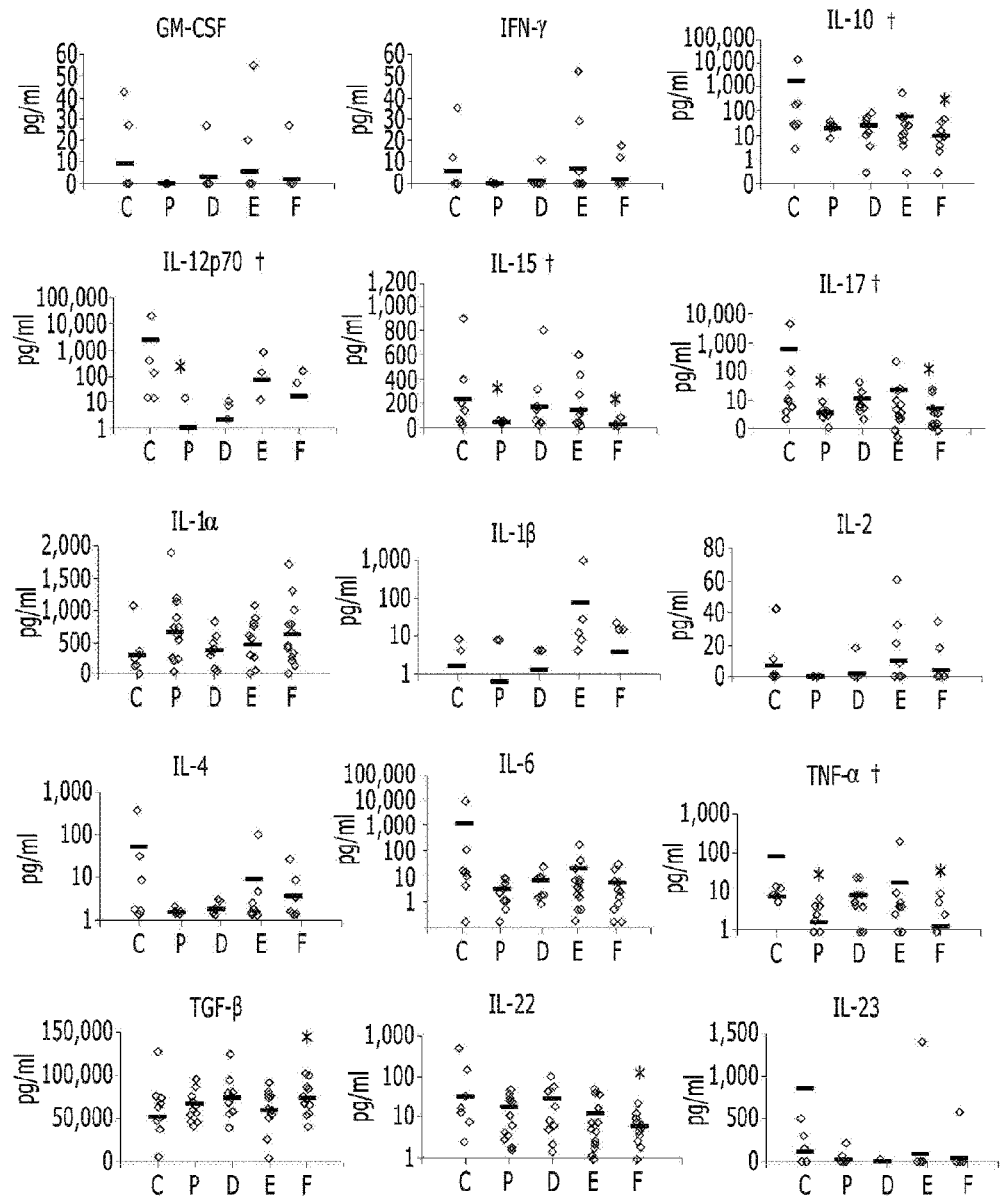
FIG. 13 shows a change in serum cytokine patterns by means of the inventive pharmaceutical composition in the disease animal model.

As shown in the table 3 above, it was identified that IL-10, IL-12, IL-15, IL-17 and TNF-α tended to decrease in the positive control group in comparison with the negative control group, and a serum concentration of IL-10, IL-12, IL-15, IL-17, TNF-α and IL-22 was decreased in the mice of the experimental groups, while a TGF-β level was increased. In particular, it was identified that IL-10, IL-15, IL-17A, TNF-α and IL-22 were significantly low and TGF-β was significantly high in the 50 mg/kg dosed experimental group in comparison with the control group (FIG. 13).

In this regard, it was reported that a serum concentration of IL-6, IL-10, IL-17, IL-23 and IFN-γ was significantly higher and a serum concentration of TGF-β was significantly lower in SLE patients than in healthy people (Document [Zickert A et al., 2015]).

Figure 14:
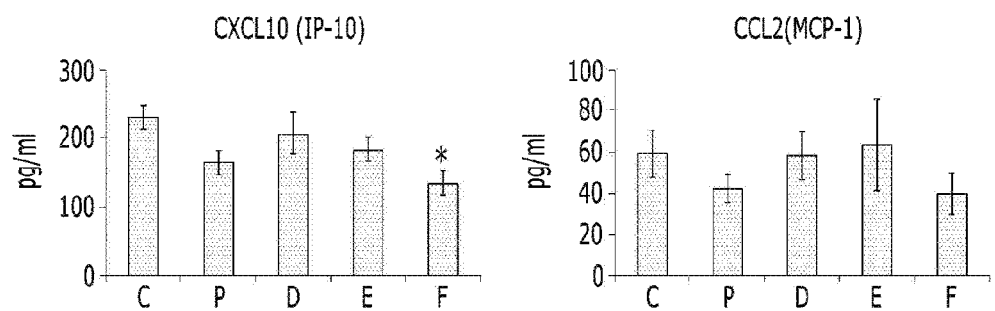
FIG. 14 shows an effect of the inventive pharmaceutical composition on reducing a serum concentration of CXCL10 and CCL2 in the disease animal model.

Meanwhile, when a level of CXCL10 (IFN-inducible protein 10, IP-10) and CCL2 (MCP-1) in serum was measured at 36 weeks old, it was identified that the level of CXCL10 in serum was decreased in all the experimental groups, and the level of CCL2 in serum was decreased in the 50 mg/kg dosed group (FIG. 14).

Example 12. T Cell Populations in Spleen in Animal Model

To evaluate a pattern of immune T cell populations in spleen in the SLE disease mouse, a ratio of CD3, CD4, CD8a and CTLA4 expressions as well as a Treg proportion/Th1, Th2, Th17 and Treg master regulator (T-bet, GATA-3, ROR-γt, Foxp3) expression patterns were measured.

To that end, splenocytes were first obtained from the spleen obtained during the mouse autopsy by means of a 70 μm cell strainer (BD), and then red blood cells were hemolyzed by means of an EL buffer and washed with FACS buffer solution (5% BSA/PBS). After that, staining was performed at a concentration recommended by a manufacturer by means of PerCP-cy5.5-conjugated anti-mouse CD3 (ebioscience, Sandiego, Calif., USA), PE-Cyanine7-conjugated anti-mouse CD8a (ebioscience), FITC-conjugated anti-CD4 (BD), APC-conjugated anti-mouse CD25 (BD), PE-conjugated anti-mouse FoxP3 (BD), PE-conjugated anti-mouse RORγt (ebioscience), PE-conjugated anti-mouse T-bet (ebioscience), PE-conjugated anti-mouse GATA-3 (ebioscience), and PE-conjugated anti-mouse CTLA4 (ebioscience) antibodies.

The splenocytes and cell surface marker antibodies were immediately reacted. Before reacting FoxP3, RORγt, T-bet and GATA3 antibodies, the splenocytes were fixed by means of a FoxP3/Transcription Factor staining buffer set, then permeabilized, and then reacted with the antibodies. A ratio of CD4:CD8 in CD3 cells as well as a ratio of CD4+CD8- cells, CD4-CD8+ cells, CD4+CD8+ cells and double negative T cells were respectively measured and compared between the groups. To identify a ratio of FoxP3, RORγt, T-bet and GATA3, which were master regulators of Treg, Th17, Th1 and Th2, a ratio of CD4+CD25+FoxP3+ cells, CD4+CD25+RORγt+ cells, CD4+CD25+ T-bet+ cells and CD4+CD25+GATA3+ cells was respectively measured.

Analysis of CD4, CD8 Expression Patterns

It was reported that a ratio of CD4-CD8- double negative T cells was increased in the peripheral blood monocytes of an SLE patient, and such cell produced inflammatory cytokines IL-17 and IFN-γ, thus contributing to the pathogenesis of kidney injuries in the SLE patient (Document [Shivakumar S et al., 1989]; Document [Crispin J C et al., 2008]).

Figure 15:
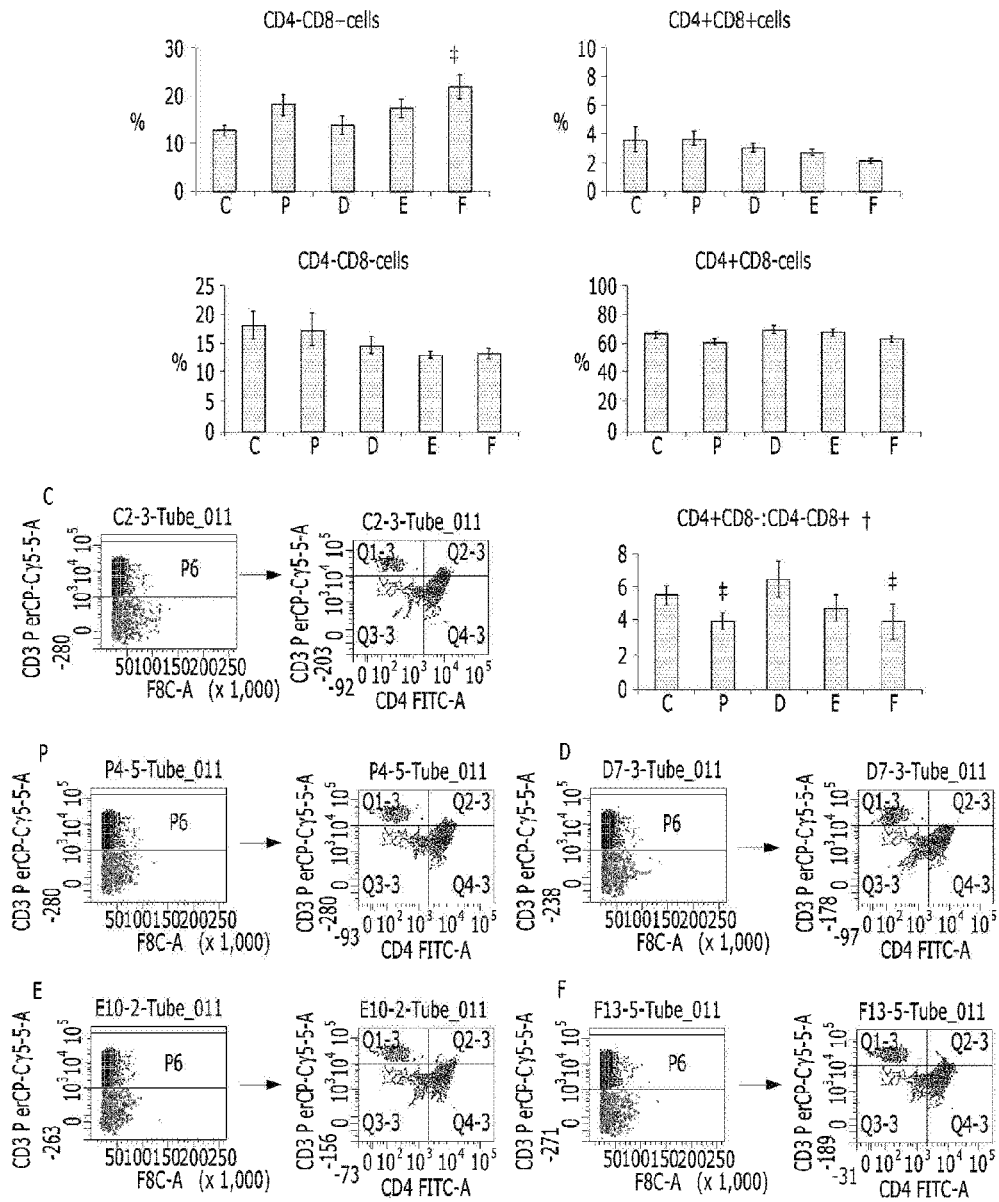
FIG. 15 shows an effect of the inventive pharmaceutical composition on a CD4 and CD8 T cell ratios in the disease animal model.

As a result of gating CD3+ cells and measuring an expression of CD4 and CD8, a ratio of CD4-CD8+ T cells was increased in the experimental groups, but a ratio of CD4-CD8- T cells was decreased on the contrary. It was shown that a ratio of CD4+CD8-: CD4-CD8+ T cells tended to decrease as an administered dose was increased in the experimental groups (FIG. 15).

Analysis of Treg, Th17, Th1 and Th2 Master Regulator Expression Patterns

Figure 16:
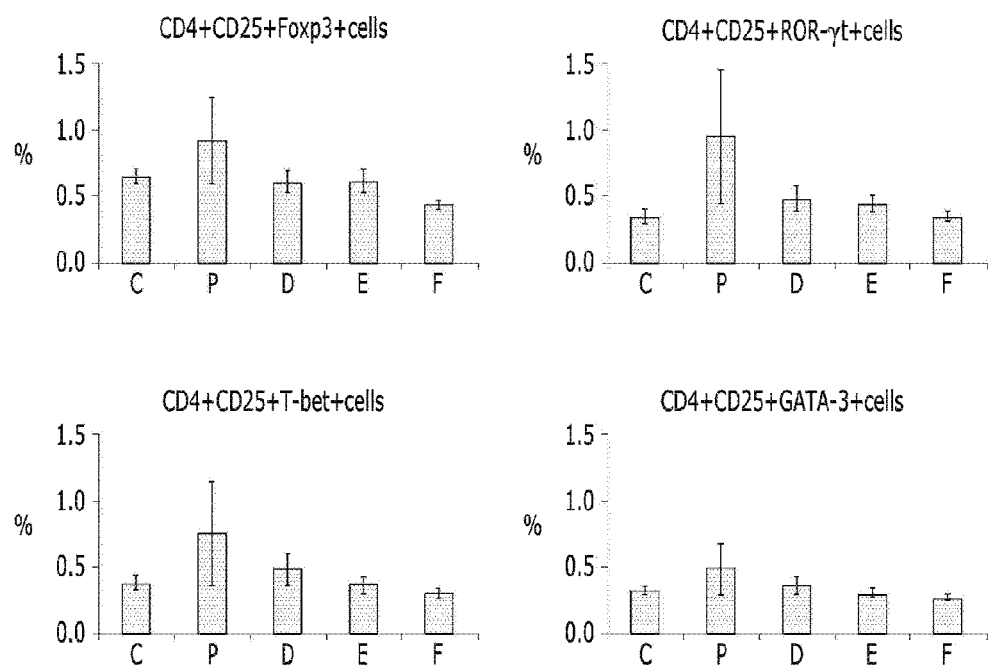
FIGS. 16 and 17 show an effect of the inventive pharmaceutical composition on CD4+CD25+ T cells in the disease animal model.

When a ratio of CD4+CD25+Foxp3+, CD4+CD25+RORγt+, CD4+CD25+ T-bet+ and CD4+CD25+GATA-3+ cells in the spleen was compared and analyzed so as to identify a degree of Foxp3, ROR-γt, T-bet and GATA-3 expressions, which were Treg, Th17, Th1 and Th2 master regulators, a significance between the groups was not observed yet (FIG. 16).

Figure 17:
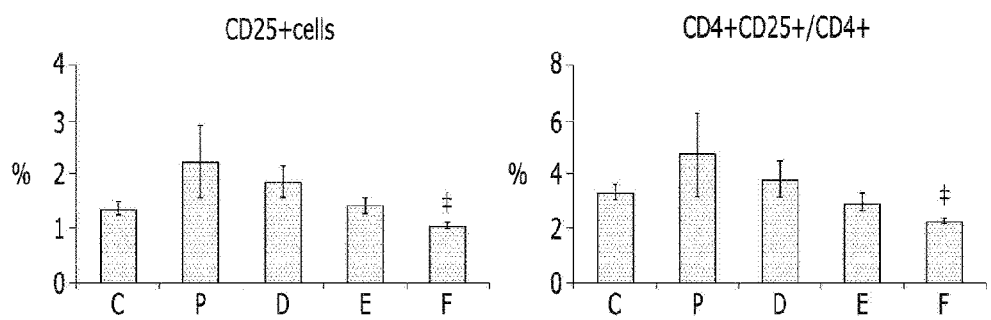

Meanwhile, a ratio of CD25+ cells was significantly lower and a ratio of CD4+CD25+ cells/CD4+ cells was also significantly lower in the 50 mg/kg dosed experimental group than in the control group (FIG. 17).

Figure 18:
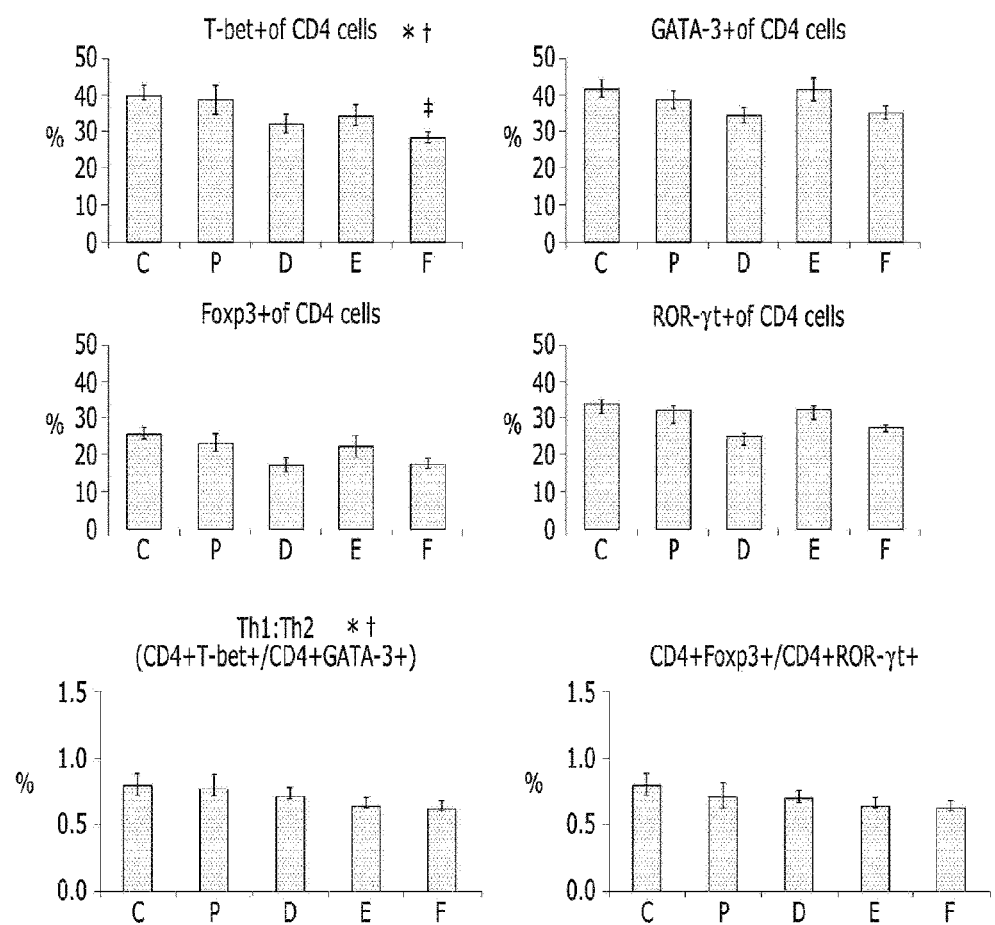
FIG. 18 shows an effect of the inventive pharmaceutical composition on an expression of $T_{reg}$, Th17, Th1, Th2 cells and master regulator in the disease animal model.

As a result of gating in CD4+ cells and investigating an expression of T-bet, GATA-3, Foxp3 and RORγt, the T-bet expression was significantly lower in the 50 mg/kg dosed experimental group than in the control group. Furthermore, it was identified that a ratio of CD4+T-bet+/CD4+GATA-3+(a ratio of Th1/Th2 master regulator expression in CD4 cells) was more significantly decreased in the 30 mg/kg and 50 mg/kg dosed experimental groups than in the control group (FIG. 18).

Analysis of CD138 Expression Pattern

Figure 19:
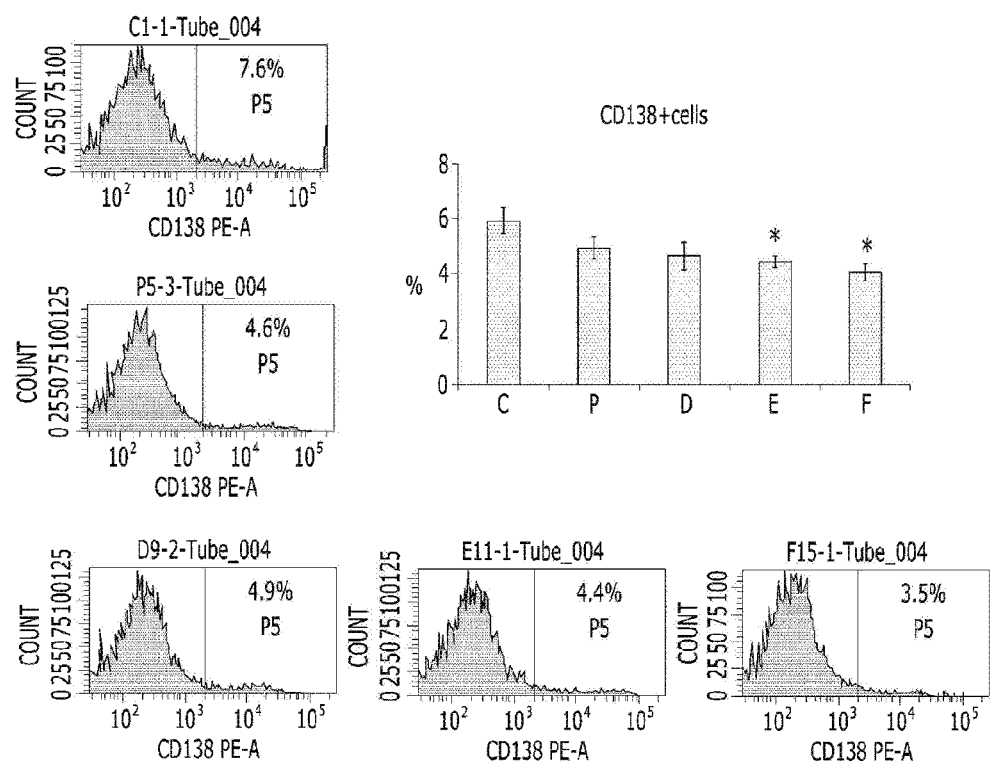
FIG. 19 shows an effect of the inventive pharmaceutical composition on CD138+ cells in the disease animal model.

It was identified that a ratio of CD138+ cells was decreased by 16.3% in the positive control group in comparison with the negative control group, but was also decreased by 21.2% in the 10 mg/kg dosed group, 25.2% in the 30 mg/kg dosed group, and 31.6% in the 50 mg/kg dosed group, respectively (FIG. 19).

Example 13. Ratio of PreB and ProB Cells in Marrow in Animal Model

A ratio of pro B (B220+, CD43+) and pre B (B220+, CD43−) cells in mouse marrow cells was measured by means of FACS. To that end, the marrow cells were obtained by flushing a femur with PBS comprising 5% BSA. After that, red blood cells were hemolyzed by means of EL buffer, then washed with FACS buffer (5% BSA/PBS), and then stained with FITC-conjugated anti-mouse CD43 antibodies (ebioscience) and PE-conjugated anti-mouse CD220 antibodies (ebioscience), such that a ratio of Pre B (B220+ CD43−) and Pro B (B220+CD43+) cells was measured.

Figure 20:
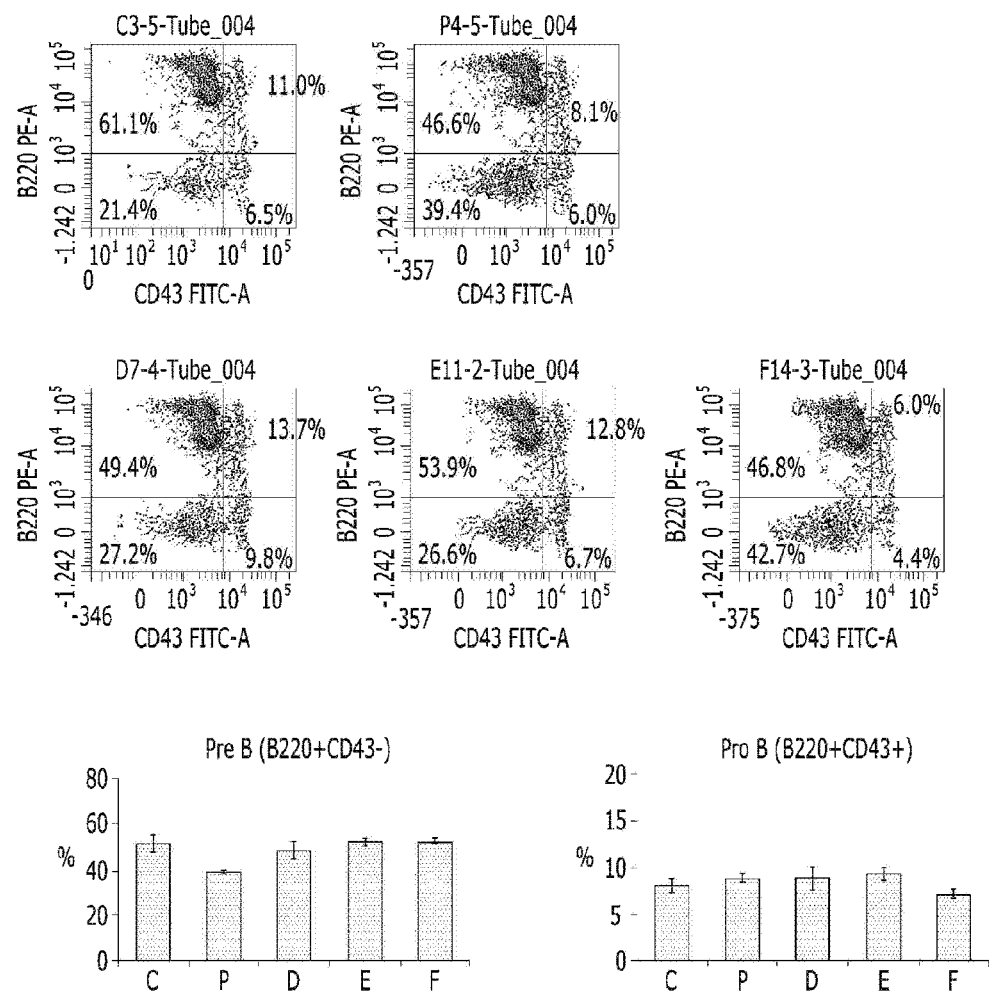
FIG. 20 shows an effect of the inventive pharmaceutical composition on PreB and ProB cells in marrow in the disease animal model.

As a result, a significant change in the ratio of pre B and pro B cells was not observed yet in the experimental groups in comparison with the control group (FIG. 20).

Example 14. Change in Immunoglobulin Isotypes in Serum in Animal Model

A concentration of immunoglobulin isotypes (IgG1, IgG2a, IgG2b, IgG3 and IgM) in the serum obtained during the mouse autopsy was measured by means of Luminex assay kit for mouse isotype (R&D systems, Minneapolis, Minn.).

Figure 21:
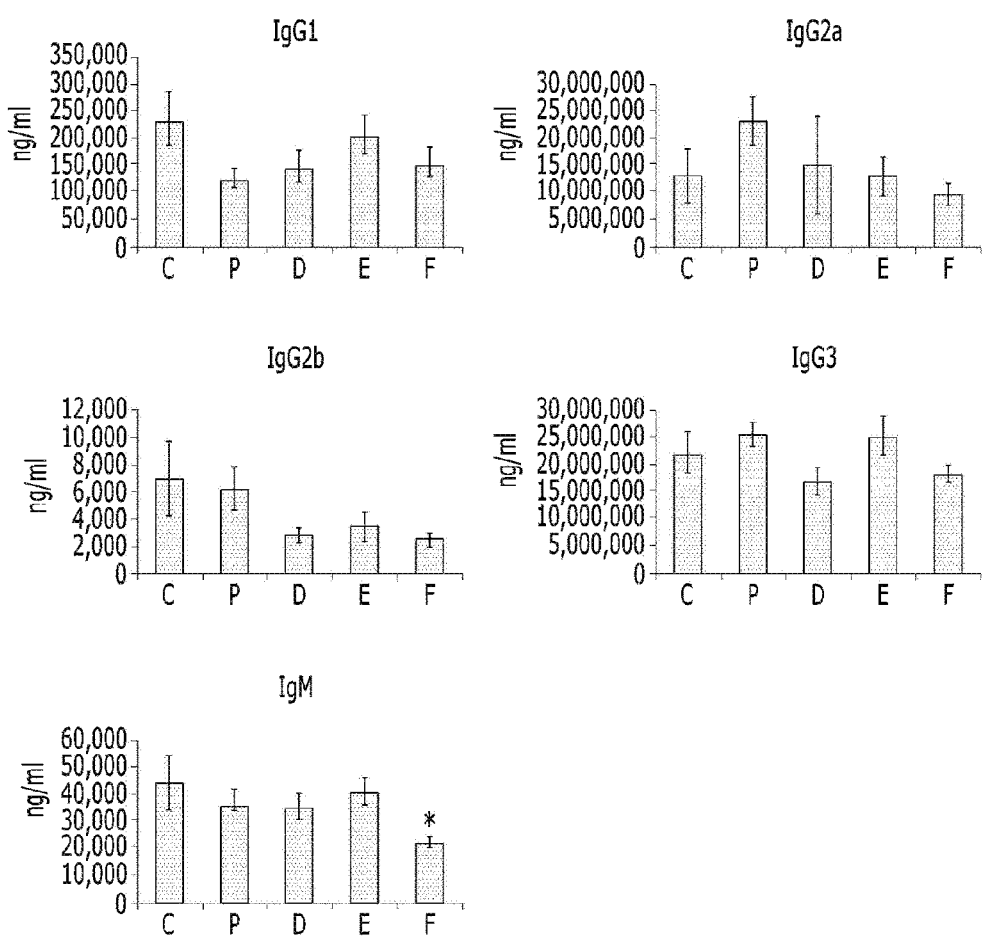
FIG. 21 shows an effect of the inventive pharmaceutical composition on a level of immunoglobulin isotypes in the disease animal model.

As a result, the concentration of IgG1, IgG2a, IgG2b, IgG3 and IgM was decreased in the 50 mg/kg dosed group in comparison with the negative control group, in particular it was identified that the concentration of IgM was remarkably decreased (FIG. 21).

Example 15. Change in Serum Chemistry in Animal Model

To identify whether there is any serum chemical change or not according to a long-term administration of the drug in the SLE animal model, the concentration of ALT, AST, ALP, total protein, albumin, total cholesterol, TG, CPK, total bilirubin and Ca in the serum obtained during the autopsy was measured by means of Dri-CHEM 3000 colorimetric analyzer (Fujifilm), wherein the results thereof are shown in a table 4.

TABLE 4

|  | C | P | D | E | F |
|---|---|---|---|---|---|
| ALT (U/l) † | 15.25 ± 1.74 | 24.09 ± 2.00* | 18.10 ± 1.72 | 20.79 ± 0.78* | 29.07 ± 3.26* |
| AST (U/l) | 39.75 ± 7.11 | 52.09 ± 4.25* | 44.20 ± 3.19 | 55.21 ± 5.17* | 59.00 ± 15.00 |
| ALP (U/l) † | 186.38 ± 14.24 | 207.45 ± 7.21 | 187.44 ± 20.75 | 155.92 ± 5.53* | 153.08 ± 4.78 |
| TBIL (mg/dl) | 0.25 ± 0.08 | 0.41 ± 0.09 | 0.22 ± 0.03 | 0.26 ± 0.03 | 0.28 ± 0.04 |
| TCHOL (mg/dl) † | 191.25 ± 25.46 | 162.09 ± 8.97 | 193.60 ± 34.55 | 140.07 ± 14.48 | 129.57 ± 8.98 |
| TG (mg/dl) | 258.88 ± 28.94 | 251.82 ± 29.19 | 241.00 ± 35.25 | 240.86 ± 56.19* | 183.29 ± 15.00 |
| Glucose (mg/dl) † | 159.38 ± 7.55 | 189.27 ± 12.23 | 162.56 ± 9.36 | 191.29 ± 7.33* | 200.23 ± 3.91* |
| Albumin (g/dl) † | 1.89 ± 0.13 | 2.52 ± 0.07* | 1.91 ± 0.14 | 2.19 ± 0.11 | 2.26 ± 0.09* |
| TP (g/dl) † | 4.71 ± 0.20 | 5.42 ± 0.11* | 4.74 ± 0.20 | 5.21 ± 0.19 | 5.35 ± 0.16* |
| CPK (U/l) | 99.38 ± 32.03 | 64.36 ± /4.26 | 86.70 ± 17.99 | 84.71 ± 8.39 | 125.86 ± 47.35 |
| Ca (mg/dl) | 10.10 ± 0.60 | 9.35 ± 0.16 | 10.08 ± 0.40 | 9.65 ± 0.19 | 9.43 ± 0.16 |

Data obtained from groups were compared using a Kruskal-Wallis (†p<0.05), *p<0.05 versus C group (Mann-Whitney U-test), ALT: alanine aminotransferase, AST: aspartate aminotransferase, ALP: alkaline phosphatase, TBIL: total bilirubin, TCHOL: total cholesterol, TG: triglyceride, TP: total protein, CPK: creatine phosphokinase)

As shown in the embodiments above, it was identified that the pharmaceutical composition according to the present invention improved a survival rate of an SLE disease mouse (FIG. 5), reduced an incidence rate of proteinuria (FIG. 6), a concentration of anti-dsDNA antibodies (FIG. 8), and a level of IgG and C3 infiltrations in kidney (FIG. 12), reduced a level of IL-10, IL-12, IL-15, IL-17a, TNFα and IL-22 in serum cytokine (FIG. 13) and a level of CXCL10 and CCL2 (FIG. 14), increased a level of TGF-β (FIG. 13), and decreased a ratio of CD4−CD8− double negative T cells, a ratio of CD4+CD8− cellular level to CD4−CD8+ cellular level (FIG. 15), a ratio of CD4+T−bet+/CD4+GATA3+(FIG. 16), a ratio of CD4+CD25+ cellular level to CD4+ cellular level (FIG. 17) and a CD138+ cellular level (FIG. 19). Based on the results above, it can be seen that the pharmaceutical composition according to the present invention has a remarkably excellent effect on treating lupus including the SLE.

While specific portions of the present invention have been described in detail above, it is apparent to those skilled in the art that such detailed descriptions are set forth to illustrate preferred exemplary embodiments only, but not construed to limit the scope of the present invention. Thus, it should be understood that the substantial scope of the present invention is defined by the accompanying claims and equivalents thereto.

The invention claimed is:

1. A method for treating lupus, comprising administering a therapeutically effective amount of a compound represented by a following formula I, an optical isomer thereof or a pharmaceutically acceptable salt thereof to a subject in need thereof

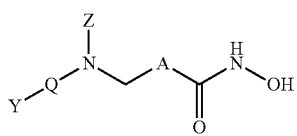

[Formula I]

wherein
A is

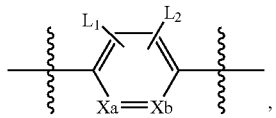

Xa and Xb are each independently CH or N,
$L_1$ and $L_2$ are each independently hydrogen, halogen, —$CF_3$ or —$C_{1-3}$ straight or branched chain alkyl,
Q is C(=O), S(=O)$_2$, S(=O) or C(=NH),
Y is selected from a following group:

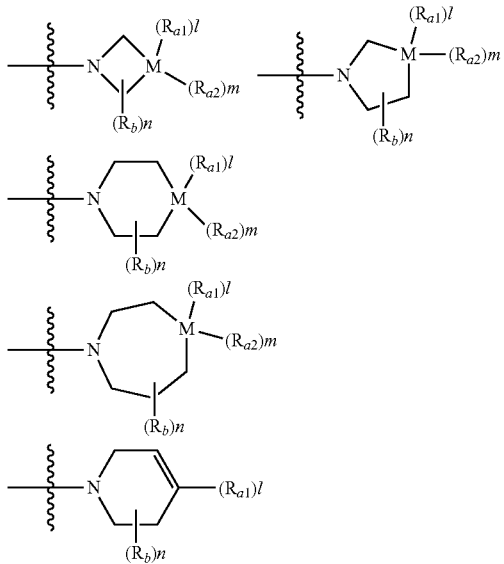

M is C, N, O, S or S(=O)$_2$, wherein, at this time, in case M is C, l and m are 1; in case M is N, l is 1 and m is 0; and in case M is O, S or S(=O)$_2$, l and m are 0,
$R_{a1}$ and $R_{a2}$ are each independently hydrogen; hydroxy; —$C_{1-4}$ straight or branched chain alkyl, which is unsubstituted or substituted with at least one halogen; —$C_{1-4}$ straight or branched chain alcohol; benzhydryl; —$C_{1-4}$ straight or branched chain alkyl, which is substituted with a saturated or unsaturated 5- to 7-membered heterocyclized compound comprising 1 to 3 heteroatoms of N, O or S as a ring member, wherein, at this time, the heterocyclized compound may be unsubstituted or at least one hydrogen may be optionally substituted with OH, OCH$_3$, CH$_3$, CH$_2$CH$_3$ or halogen; a saturated or unsaturated 5- to 7-membered heterocyclized compound comprising 1 to 3 heteroatoms of N, O or S as a ring member, wherein, at this time, the heterocyclized compound may be unsubstituted or at least one hydrogen may be optionally substituted with OH, OCH$_3$, CH$_3$, CH$_2$CH$_3$ or halogen; phenyl, wherein it is unsubstituted or at least one hydrogen is substituted with halogen, $C_{1-4}$ alkoxy, $C_{1-2}$ alkyl or hydroxy; benzyl, wherein it is unsubstituted or at least one hydrogen is substituted with halogen, $C_{1-4}$ alkoxy, $C_{1-2}$ alkyl or hydroxy; —S(=O)$_2$CH$_3$; halogen; —$C_{1-6}$ straight or branched chain alkoxy; —$C_{2-6}$ alkoxyalkyl; —C(=O)R$_x$, wherein R$_x$ is straight or branched chain $C_{1-3}$ alkyl or $C_{3-10}$ cycloalkyl;

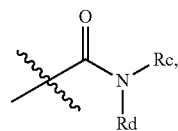

wherein R$_c$ and R$_d$ are each independently hydrogen, $C_{1-3}$ straight or branched chain alkyl; and

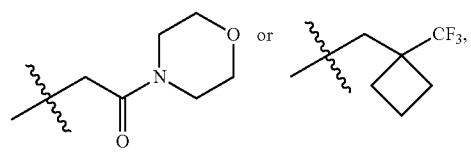 [SMILES: *CC(=O)N1CCOCC1 ; *CC1(C(F)(F)F)CCC1]

n is an integer of 0, 1 or 2,
R$_b$ is hydrogen; hydroxy; —$C_{1-6}$ straight or branched chain alkyl, wherein it is unsubstituted or at least one hydrogen is substituted with halogen; —C(=O)CH$_3$; —$C_{1-4}$ straight or branched chain hydroxyalkyl; —$C_{1-6}$ straight or branched chain alkoxy; —$C_{2-6}$ straight or branched chain alkoxyalkyl; —CF$_3$; halogen; or

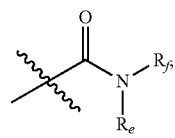

R$_e$ and R$_f$ are each independently hydrogen or —$C_{1-3}$ straight or branched chain alkyl,
Z is selected from a following group:

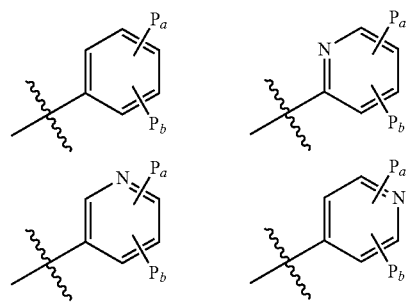

-continued

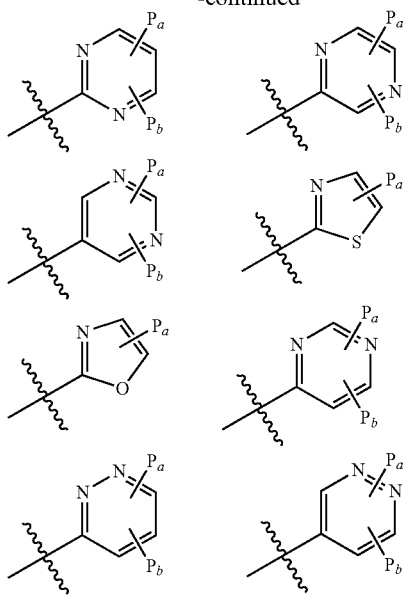

$P_a$ and $P_b$ are each independently

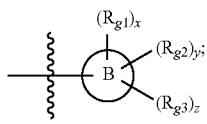

hydrogen; hydroxy; —$C_{1-4}$ straight or branched chain alkyl, wherein it is unsubstituted or at least one hydrogen is substituted with halogen; halogen; —$CF_3$; —$OCF_3$; —CN; —$C_{1-6}$ straight or branched chain alkoxy; —$C_{2-6}$ straight or branched chain alkyl alkoxy; —$CH_2F$; or —$C_{1-3}$ alcohol, where

is phenyl, pyridine, pyrimidine, thiazole, indole, indazole, piperazine, quinoline, furan, tetrahydropyridine, piperidine or a ring selected from a following group:

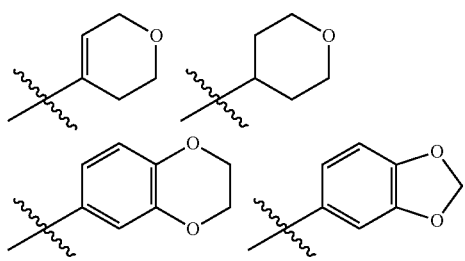

x, y and z are each independently an integer of 0 or 1, $R_{g1}$, $R_{g2}$ and $R_{g3}$ are each independently hydrogen; hydroxy; —$C_{1-3}$ alkyl; —$CF_3$; —$C_{1-6}$ straight or branched chain alkoxy; —$C_{2-6}$ straight or branched chain alkyl alkoxy; —C(=O)$CH_3$; —$C_{1-4}$ straight or branched chain hydroxyalkyl; —N(CH$_3$)$_2$; halogen; phenyl; —S((=O)$_2$)$CH_3$; or selected from a following group:

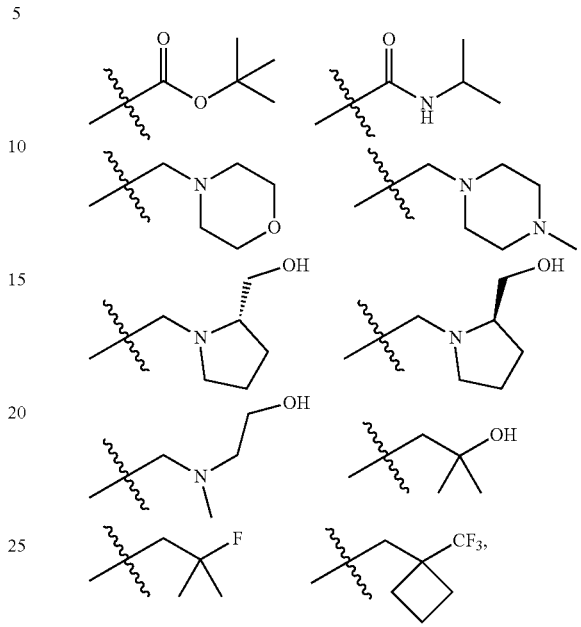

wherein the lupus is selected from a group consisting of systemic lupus erythematosus (SLE), systemic lupus, discoid lupus, drug induced lupus, neonatal lupus, lupus nephritis and glomerulonephritis.

2. The method according to claim 1, wherein the compound represented by the formula I above is a compound represented by a following formula Ia:

[Formula Ia]

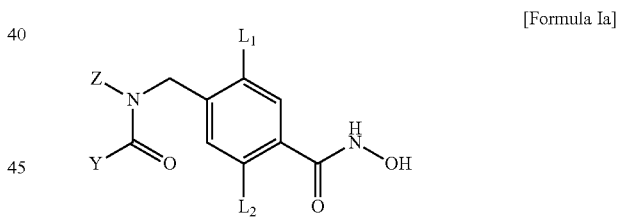

wherein
$L_1$ and $L_2$ are each independently hydrogen or halogen, Y is,

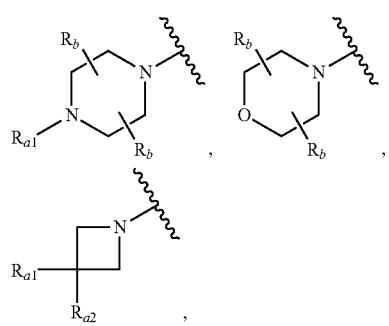

$R_{a1}$, $R_{a2}$ and $R_b$ are each independently as defined in claim 1,

Z is phenyl or pyridinyl, wherein at least one hydrogen of phenyl or pyridinyl may be substituted with halogen, $CF_3$ or $CH_2F$.

3. The method according to claim 2, wherein the compound represented by the formula Ia above is

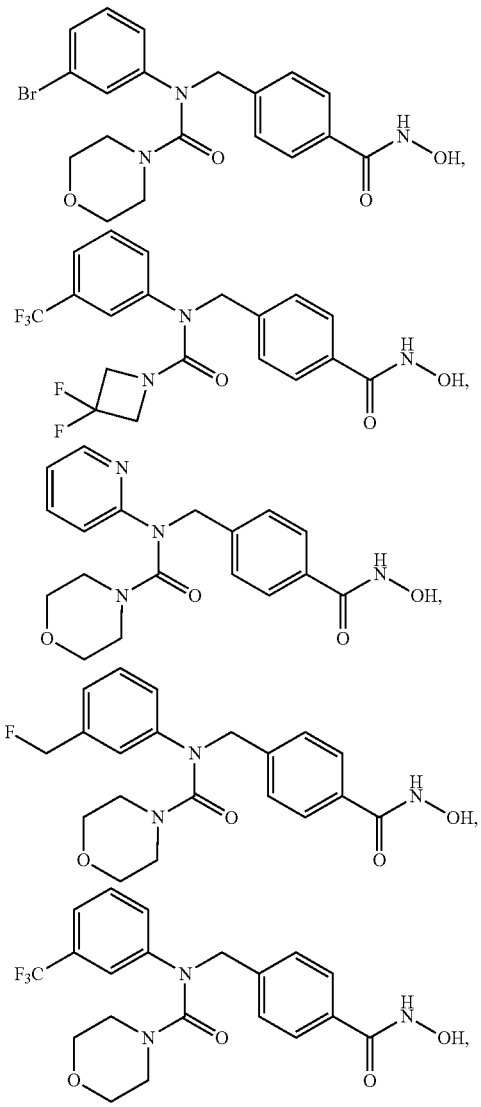

-continued

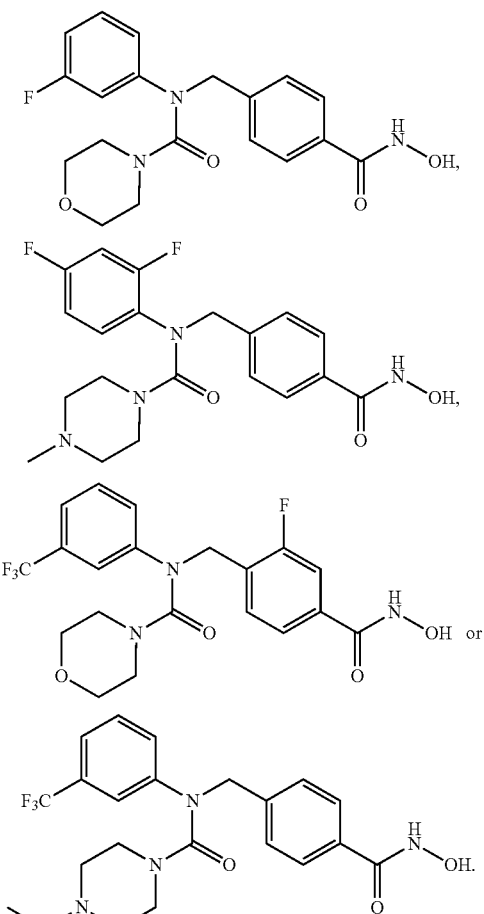

4. The method according to claim 1, wherein said compound, an optical isomer thereof or pharmaceutically acceptable salt thereof reduces a serum concentration of anti-dsDNA antibodies.

5. The method according to claim 1, wherein said compound, an optical isomer thereof or pharmaceutically acceptable salt thereof suppresses a production of proteinuria.

6. The method according to claim 1, wherein said compound, an optical isomer thereof or pharmaceutically acceptable salt thereof suppresses a production of TNFα in an inflammatory reaction.

* * * * *